US012735479B2

(12) United States Patent
Jia

(10) Patent No.: US 12,735,479 B2
(45) Date of Patent: Sep. 15, 2026

(54) MONOCLONAL ANTIBODIES AGAINST CLDN18.2 AND Fc-ENGINEERED VERSIONS THEREOF

(71) Applicant: Shijiazhuang Yiling Pharmaceutical Co., Ltd., Shijiazhuang (CN)

(72) Inventor: Zhenhua Jia, Shijiazhuang (CN)

(73) Assignee: Shijiazhuang Yiling Pharmaceutical Co., Ltd., Shijiazhuang (CN)

( * ) Notice: Subject to any disclaimer, the term of this patent is extended or adjusted under 35 U.S.C. 154(b) by 496 days.

(21) Appl. No.: 18/565,360

(22) PCT Filed: May 30, 2022

(86) PCT No.: PCT/CN2022/095841

§ 371 (c)(1),
(2) Date: Nov. 29, 2023

(87) PCT Pub. No.: WO2022/253156

PCT Pub. Date: Dec. 8, 2022

(65) Prior Publication Data

US 2025/0263482 A1 Aug. 21, 2025

(30) Foreign Application Priority Data

May 31, 2021 (WO) ................ PCT/CN2021/097239
May 31, 2021 (WO) ................ PCT/CN2021/097240
Jul. 16, 2021 (WO) ................ PCT/CN2021/106783
Jul. 16, 2021 (WO) ................ PCT/CN2021/106784

(51) Int. Cl.
*C07K 16/28* (2006.01)

(52) U.S. Cl.
CPC .......... *C07K 16/28* (2013.01); *C07K 2317/24* (2013.01); *C07K 2317/31* (2013.01); *C07K 2317/33* (2013.01); *C07K 2317/52* (2013.01); *C07K 2317/565* (2013.01); *C07K 2317/71* (2013.01); *C07K 2317/72* (2013.01); *C07K 2317/732* (2013.01); *C07K 2317/734* (2013.01); *C07K 2317/77* (2013.01); *C07K 2317/92* (2013.01)

(58) Field of Classification Search
None
See application file for complete search history.

(56) References Cited

U.S. PATENT DOCUMENTS

2021/0230272 A1 7/2021 Liu
2022/0235129 A1 7/2022 Jin et al.
2022/0332814 A1 10/2022 Jheng et al.

FOREIGN PATENT DOCUMENTS

CN 112830969 A 5/2021
WO 2019173420 A1 9/2019
WO 2019242505 A1 12/2019
WO 2020038404 A1 2/2020
WO 2020147321 A1 7/2020
WO 2020160560 A2 8/2020
WO 2021008463 A1 1/2021
WO 2021032157 A1 2/2021
WO 2021047599 A1 3/2021
WO 2021063336 A1 4/2021

OTHER PUBLICATIONS

International Search Report & Written Opinion issued in PCT/CN2022/095841, mailed Sep. 1, 2022 [9 pages].
Lin et al., “Abstract B73: Development of anti-human CLDN18.2 monoclonal antibody as cancer therapeutics,” Canc. Immunol. Res. 8(4 Supplement):B73 (2020), 5 pages.
Singh et al., “Anti-claudin 18.2 Antibody as new targeted therapy for advanced gastric cancer,” J. Hem. Onc. 10:105 (2017), 5 pages.
Zhang et al., “Evaluation and reflection on claudin 18.2 targeting therapy in advanced gastric cancer,” Chin. J. Cancer. Res. 32(2):263-270 (2020), 8 pages.

*Primary Examiner* — Maher M Haddad
*Assistant Examiner* — Alan Alfano
(74) *Attorney, Agent, or Firm* — Ice Miller LLP

(57) ABSTRACT

A panel of monoclonal antibodies which specifically bind to CLDN18.2 and do not specifically bind to CLDN18.1, and optionally have an engineered Fc region is provided.

17 Claims, 11 Drawing Sheets

Specification includes a Sequence Listing.

Kabat

```
HEAVY CHAIN Variable region (mouse)

YL-01-19-01   QVQLQQSGAELVRPGTSVKVSCKASGYAFTNYLIEWVKQRPGQGLEWIGVINPGSGGTNY   60
YL-01-19-02   EVQLQQSGPELEKPGASVKISCKASGYSFTGYKMNWVKQSNGKSLEWIGNIDPYYGGTTY   60
YL-01-19-03   QIQLVQSGPELRKPGETVKISCKASGFPFTTDGMSWVKQAPGKGLKWMGWINTYSGVPTY   60
YL-01-19-04   EVQLQQSGPELEKPGASVKISCKASGYSFTGYKMNWVKQSNGESLEWIGNIDPYYGDTTY   60
               **  *   *  **  **  *      **  *****    ** ** *** * **** ***

YL-01-19-01   NEKFKGKATLTADKSSNTAYMQLSSLTSEDSAVYFCARVYYGNSFGYWGQGTLVTVSA    118
YL-01-19-02   NQKFKGKATLTVDKSSSTAYMQLKSLTSEDSAVYYCARYGKGNTMDYWGQGTSVTVSS    118
YL-01-19-03   ADDFKGRVAFSLETSASTAYLQIKNLKNEDTATYFCARFRRGNALDNWGQGTSVTVSS    118
YL-01-19-04   TQKFKGKATFTVDTSSSTAYMQLKSLTSEDSAVYFCARYNRGNTMDYWGQGTSVTVSS    118
               ***   ******** **   * *** **  * * *   ***  ****     *   *

LIGHT CHAIN Variable region (mouse)

YL-G1-19-01   DIVMTQSPSSLTVTAGEKVTMSCKSSQSLLNSGNQKNYLTWYQQKPGQPPKLLIYWASTR   60
YL-G1-19-02   DIVMTQSPSSLTVTAGEKVTMSCKSSQSLLNSGNQKNYLTWYQQRPGQPPKLLIYWASTR   60
YL-G1-19-03   DIVMTQSPSSLTVTAGEKVTMSCKSSQSLLNSGNQKNYLTWYQQKPGQPPKLLIYWASTR   60
YL-G1-19-04   DIVMTQSPSSLTVTAGEKVTLSCKSSQSLLNSGNQKNYLTWYQQRPGQPPKLLIYWASTR   60
                                   *                       *

YL-G1-19-01   ESGVPDRFTGSGSGTDFTLTISSVQAEDLAVYYCQNEYFYPFTFGSGTKLEIK         113
YL-G1-19-02   ESGVPVRFTGSGSGTDFTLTISSVQAEDLAVYYCQNAYIYPLTFGTGTKLELK         113
YL-G1-19-03   ESGVPDRFTGSGSGTDFTLTISSVQAEDLAIYYCQNNYFYPLTFGAGTRLELK         113
YL-G1-19-04   ESGVPVRFTGSGSGADFTLTISSVQAEDLAVYFCQNAYFYPLTFGTGTKLELR         113
                    *        *               * *   * *  *   *  *  **
```

Figure 1A

IMGT

```
HEAVY CHAIN Variable region (mouse)

YL-01-19-01  QVQLQQSGAELVRPGTSVKVSCKASGYAFTNYLIEWVKQRPGQGLEWIGVINPGSGGTNY   60
YL-01-19-02  EVQLQQSGPELEKPGASVKISCKASGYSFTGYKMNWVKQSNGKSLEWIGNIDPYYGGTTY   60
YL-01-19-03  QIQLVQSGPELRKPGETVKISCKASGFPFTTDGMSWVKQAPGKGLKWMGWINTYSGVPTY   60
YL-01-19-04  EVQLQQSGPELEKPGASVKISCKASGYSFTGYKMNWVKQSNGESLEWIGNIDPYYGDTTY   60
              **  *   *  **  **  *      **  *****    ** ** *** * **** ***

YL-01-19-01  NEKFKGKATLTADKSSNTAYMQLSSLTSEDSAVYFCARVYYGNSFGYWGQGTLVTVSA    118
YL-01-19-02  NQKFKGKATLTVDKSSSTAYMQLKSLTSEDSAVYYCARYGKGNTMDYWGQGTSVTVSS    118
YL-01-19-03  ADDFKGRVAFSLETSASTAYLQIKNLKNEDTATYFCARFRRGNALDNWGQGTSVTVSS    118
YL-01-19-04  TQKFKGKATFTVDTSSSTAYMQLKSLTSEDSAVYFCARYNRGNTMDYWGQGTSVTVSS    118
              ***   ******** **   * *** **  * * *   ***  ****     *    *


LIGHT CHAIN Variable region (mouse)

YL-G1-19-01  DIVMTQSPSSLTVTAGEKVTMSCKSSQSLLNSGNQKNYLTWYQQKPGQPPKLLIYWASTR   60
YL-G1-19-02  DIVMTQSPSSLTVTAGEKVTMSCKSSQSLLNSGNQKNYLTWYQQRPGQPPKLLIYWASTR   60
YL-G1-19-03  DIVMTQSPSSLTVTAGEKVTMSCKSSQSLLNSGNQKNYLTWYQQKPGQPPKLLIYWASTR   60
YL-G1-19-04  DIVMTQSPSSLTVTAGEKVTLSCKSSQSLLNSGNQKNYLTWYQQRPGQPPKLLIYWASTR   60
                                  *                       *

YL-G1-19-01  ESGVPDRFTGSGSGTDFTLTISSVQAEDLAVYYCQNEYFYPFTFGSGTKLEIK   113
YL-G1-19-02  ESGVPVRFTGSGSGTDFTLTISSVQAEDLAVYYCQNAYIYPLTFGTGTKLELK   113
YL-G1-19-03  ESGVPDRFTGSGSGTDFTLTISSVQAEDLAIYYCQNNYFYPLTFGAGTRLELK   113
YL-G1-19-04  ESGVPVRFTGSGSGADFTLTISSVQAEDLAVYFCQNAYFYPLTFGTGTKLELR   113
                   *        *               * *   * *  *   *  *  **
```

Figure 1B

Chothia

```
HEAVY CHAIN Variable region (mouse)
YL-G1-19-01   QVQLQQSGAELVRPGTSVKVSCKASGYAFTNYLIEWVKQRPGQGLEWIGVINPGSGGTNY   60
YL-G1-19-02   EVQLQQSGPELEKPGASVKISCKASGYSFTGYKMNWVKQSNGKSLEWIGNIDPYYGGTTY   60
YL-G1-19-03   QIQLVQSGPELRKPGETVKISCKASGFPFTTDGMSWVKQAPGKGLKWMGWINTYSGVPTY   60
YL-G1-19-04   EVQLQQSGPELEKPGASVKISCKASGYSFTGYKMNWVKQSNGESLEWIGNIDPYYGDTTY   60
                ** *  * ** ** *    ** *****   ** ** *** * **** ***

YL-G1-19-01   NEKFKGKATLTADKSSNTAYMQLSSLTSEDSAVYFCARVYYGNSFGYWGQGTLVTVSA    118
YL-G1-19-02   NQKFKGKATLTVDKSSSTAYMQLKSLTSEDSAVYYCARYGKGNTMDYWGQGTSVTVSS    118
YL-G1-19-03   ADDFKGRVAFSLETSASTAYLQIKNLKNEDTATYFCARFRRGNALDNWGQGTSVTVSS    118
YL-G1-19-04   TQKFKGKATFTVDTSSSTAYMQLKSLTSEDSAVYFCARYNRGNTMDYWGQGTSVTVSS    118
               ***   ******** **   * *** **  * * *  ***  ****     *    *

LIGHT CHAIN Variable region (mouse)
YL-G1-19-01   DIVMTQSPSSLTVTAGEKVTMSCKSSQSLLNSGNQKNYLTWYQQKPGQPPKLLIYWASTR   60
YL-G1-19-02   DIVMTQSPSSLTVTAGEKVTMSCKSSQSLLNSGNQKNYLTWYQQRPGQPPKLLIYWASTR   60
YL-G1-19-03   DIVMTQSPSSLTVTAGEKVTMSCKSSQSLLNSGNQKNYLTWYQQKPGQPPKLLIYWASTR   60
YL-G1-19-04   DIVMTQSPSSLTVTAGEKVTLSCKSSQSLLNSGNQKNYLTWYQQRPGQPPKLLIYWASTR   60
                                  *                       *

YL-G1-19-01   ESGVPDRFTGSGSGTDFTLTISSVQAEDLAVYYCQNEYFYPFTFGSGTKLEIK         113
YL-G1-19-02   ESGVPVRFTGSGSGTDFTLTISSVQAEDLAVYYCQNAYIYPLTFGTGTKLELK         113
YL-G1-19-03   ESGVPDRFTGSGSGTDFTLTISSVQAEDLAIYYCQNNYFYPLTFGAGTRLELK         113
YL-G1-19-04   ESGVPVRFTGSGSGADFTLTISSVQAEDLAVYFCQNAYFYPLTFGTGTKLELR         113
                   *    *        * *  * * *  *  *  **
```

Figure 1C

Contact

HEAVY CHAIN Variable region (mouse)

```
YL-01-19-01  QVQLQQSGAELVRPGTSVKVSCKASGYAFTNYLIEWVKQRPGQGLEWIGVINPGSGGTNY    60
YL-01-19-02  EVQLQQSGPELEKPGASVKISCKASGYSFTGYKMNWVKQSNGKSLEWIGNIDPYYGGTTY    60
YL-01-19-03  QIQLVQSGPELRKPGETVKISCKASGFPFTTDGMSWVKQAPGKGLKWMGWINTYSGVPTY    60
YL-01-19-04  EVQLQQSGPELEKPGASVKISCKASGYSFTGYKMNWVKQSNGESLEWIGNIDPYYGDTTY    60
              **  *   *  **  **  *      **  *****    ** ** *** * **** ***

YL-01-19-01  NEKFKGKATLTADKSSNTAYMQLSSLTSEDSAVYFCARVYYGNSFGYWGQGTLVTVSA     118
YL-01-19-02  NQKFKGKATLTVDKSSSTAYMQLKSLTSEDSAVYYCARYGKGNTMDYWGQGTSVTVSS     118
YL-01-19-03  ADDFKGRVAFSLETSASTAYLQIKNLKNEDTATYFCARFRRGNALDNWGQGTSVTVSS     118
YL-01-19-04  TQKFKGKATFTVDTSSSTAYMQLKSLTSEDSAVYFCARYNRGNTMDYWGQGTSVTVSS     118
              ***   ******** **   * *** **  * * *   ***  ****      *    *
```

LIGHT CHAIN Variable region (mouse)

```
YL-G1-19-01  DIVMTQSPSSLTVTAGEKVTMSCKSSQSLLNSGNQKNYLTWYQQKPGQPPKLLIYWASTR    60
YL-G1-19-02  DIVMTQSPSSLTVTAGEKVTMSCKSSQSLLNSGNQKNYLTWYQQRPGQPPKLLIYWASTR    60
YL-G1-19-03  DIVMTQSPSSLTVTAGEKVTMSCKSSQSLLNSGNQKNYLTWYQQKPGQPPKLLIYWASTR    60
YL-G1-19-04  DIVMTQSPSSLTVTAGEKVTLSCKSSQSLLNSGNQKNYLTWYQQRPGQPPKLLIYWASTR    60
                                  *                       *

YL-G1-19-01  ESGVPDRFTGSGSGTDFTLTISSVQAEDLAVYYCQNEYFYPFTFGSGTKLEIK          113
YL-G1-19-02  ESGVPVRFTGSGSGTDFTLTISSVQAEDLAVYYCQNAYIYPLTFGTGTKLELK          113
YL-G1-19-03  ESGVPDRFTGSGSGTDFTLTISSVQAEDLAIYYCQNNYFYPLTFGAGTRLELK          113
YL-G1-19-04  ESGVPVRFTGSGSGADFTLTISSVQAEDLAVYFCQNAYFYPLTFGTGTKLELR          113
                   *        *               * *   * *  *   *  *  **
```

Figure 1D

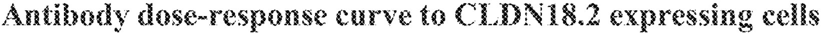
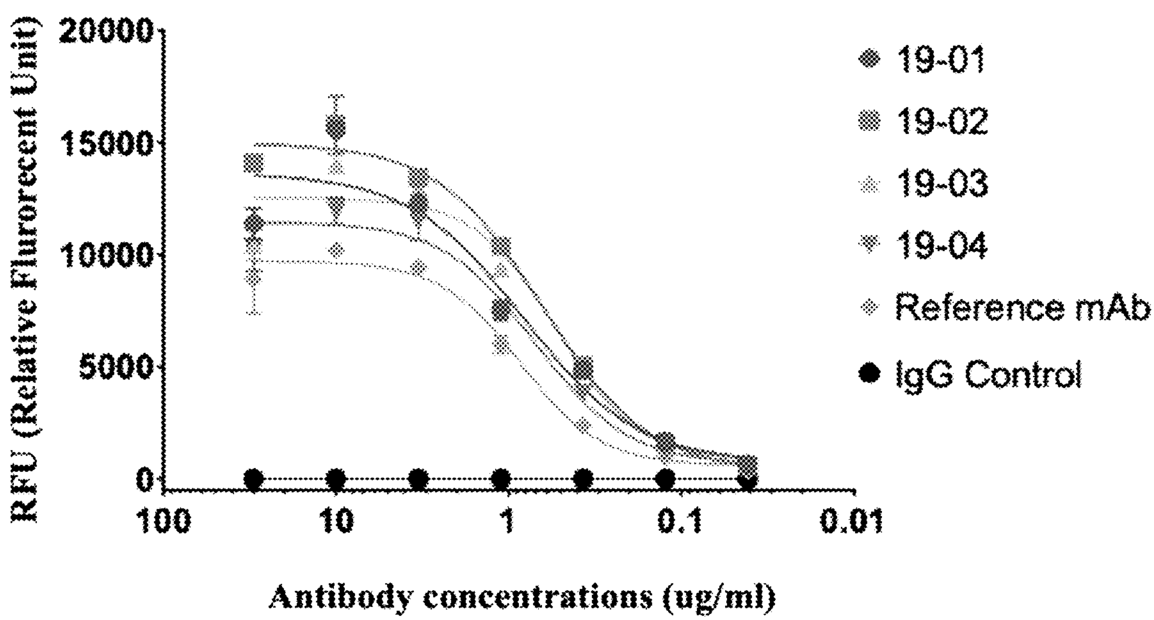
Figure 2
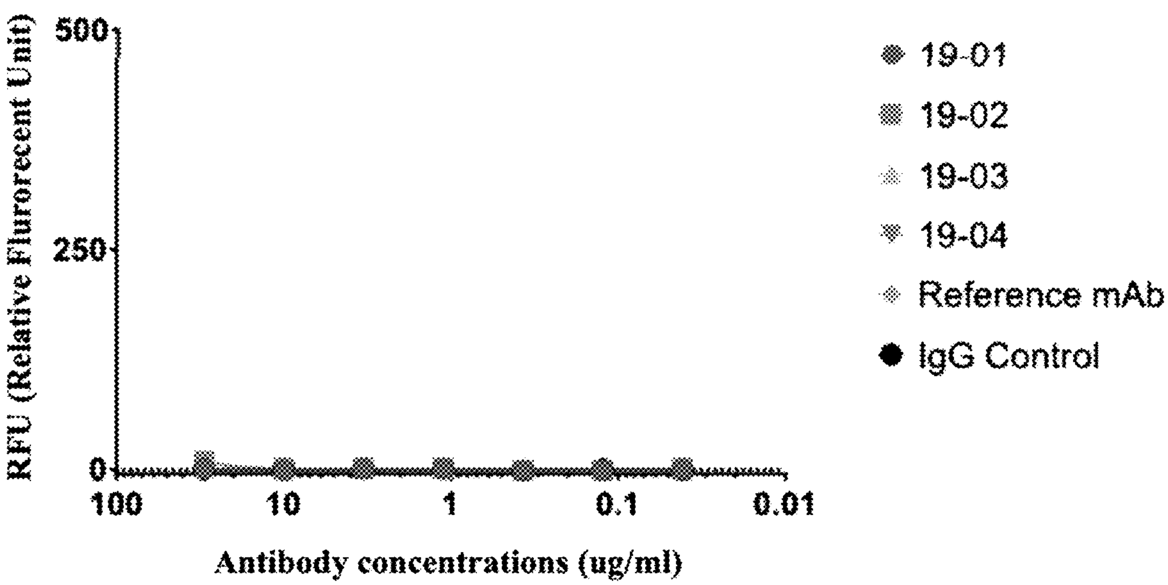
Figure 3

A.
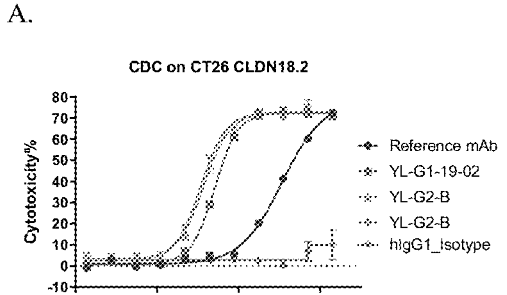
B.
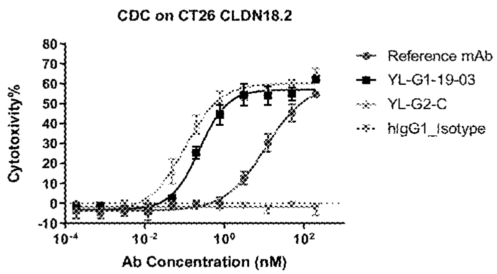
C.
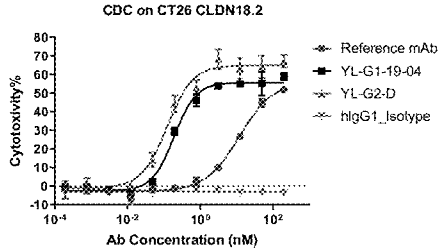
Figure 11
A.
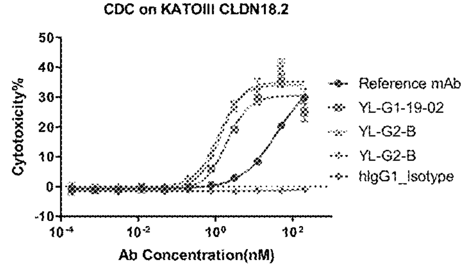
B.
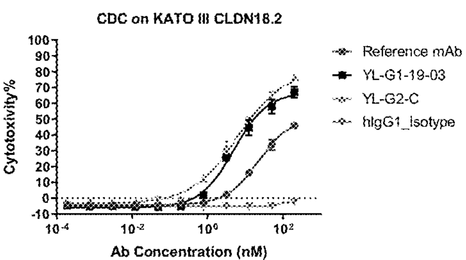
C.
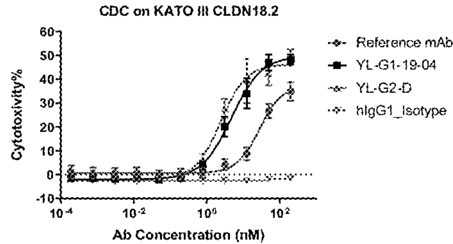
Figure 12

A.
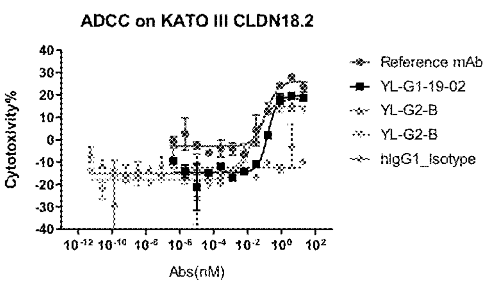
B.
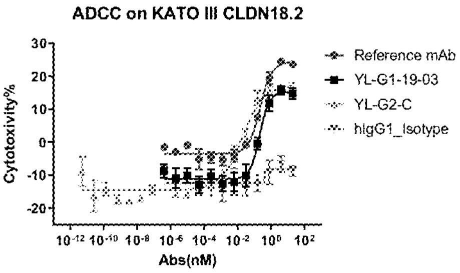
C.
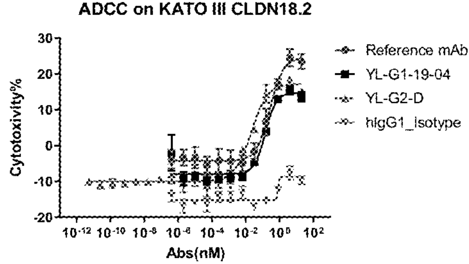
Figure 13
A.
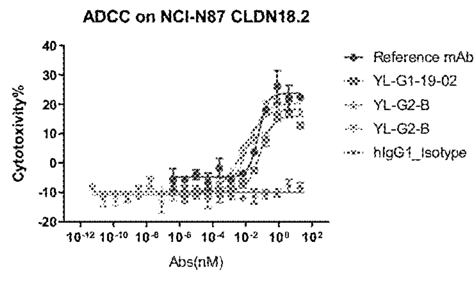
B.
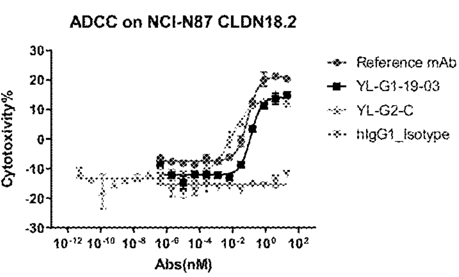
C.
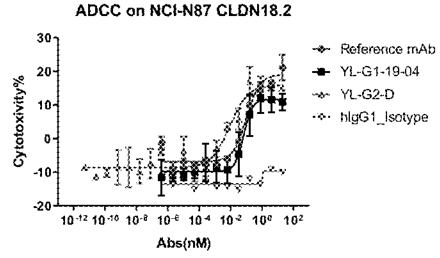
Figure 14

SEQUENCE LISTING

```
<160> NUMBER OF SEQ ID NOS: 58

<210> SEQ ID NO 1
<211> LENGTH: 118
<212> TYPE: PRT
<213> ORGANISM: Artificial Sequence
<220> FEATURE:
<223> OTHER INFORMATION: Synthetic Construct

<400> SEQUENCE: 1

Gln Val Gln Leu Gln Gln Ser Gly Ala Glu Leu Val Arg Pro Gly Thr
1               5                   10                  15

Ser Val Lys Val Ser Cys Lys Ala Ser Gly Tyr Ala Phe Thr Asn Tyr
            20                  25                  30

Leu Ile Glu Trp Val Lys Gln Arg Pro Gly Gln Gly Leu Glu Trp Ile
        35                  40                  45

Gly Val Ile Asn Pro Gly Ser Gly Gly Thr Asn Tyr Asn Glu Lys Phe
    50                  55                  60

Lys Gly Lys Ala Thr Leu Thr Ala Asp Lys Ser Ser Asn Thr Ala Tyr
```

```
65                  70                  75                  80

Met Gln Leu Ser Ser Leu Thr Ser Glu Asp Ser Ala Val Tyr Phe Cys
                85                  90                  95

Ala Arg Val Tyr Tyr Gly Asn Ser Phe Gly Tyr Trp Gly Gln Gly Thr
            100                 105                 110

Leu Val Thr Val Ser Ala
        115


<210> SEQ ID NO 2
<211> LENGTH: 113
<212> TYPE: PRT
<213> ORGANISM: Artificial Sequence
<220> FEATURE:
<223> OTHER INFORMATION: Synthetic Construct

<400> SEQUENCE: 2

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Glu Tyr Phe Tyr Pro Phe Thr Phe Gly Ser Gly Thr Lys Leu Glu Ile
            100                 105                 110

Lys


<210> SEQ ID NO 3
<211> LENGTH: 118
<212> TYPE: PRT
<213> ORGANISM: Artificial Sequence
<220> FEATURE:
<223> OTHER INFORMATION: Synthetic Construct

<400> SEQUENCE: 3

Glu Val Gln Leu Gln Gln Ser Gly Pro Glu Leu Glu Lys Pro Gly Ala
1               5                   10                  15

Ser Val Lys Ile Ser Cys Lys Ala Ser Gly Tyr Ser Phe Thr Gly Tyr
            20                  25                  30

Lys Met Asn Trp Val Lys Gln Ser Asn Gly Lys Ser Leu Glu Trp Ile
        35                  40                  45

Gly Asn Ile Asp Pro Tyr Tyr Gly Gly Thr Thr Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Lys Ser Leu Thr Ser Glu Asp Ser Ala Val Tyr Tyr Cys
                85                  90                  95

Ala Arg Tyr Gly Lys Gly Asn Thr Met Asp Tyr Trp Gly Gln Gly Thr
            100                 105                 110

Ser Val Thr Val Ser Ser
        115
```

```
<210> SEQ ID NO 4
<211> LENGTH: 113
<212> TYPE: PRT
<213> ORGANISM: Artificial Sequence
<220> FEATURE:
<223> OTHER INFORMATION: Synthetic Construct

<400> SEQUENCE: 4

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Arg Pro Gly Gln
        35                  40                  45

Pro Pro Lys Leu Leu Ile Tyr Trp Ala Ser Thr Arg Glu Ser Gly Val
    50                  55                  60

Pro Val Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Ala Tyr Ile Tyr Pro Leu Thr Phe Gly Thr Gly Thr Lys Leu Glu Leu
            100                 105                 110

Lys


<210> SEQ ID NO 5
<211> LENGTH: 118
<212> TYPE: PRT
<213> ORGANISM: Artificial Sequence
<220> FEATURE:
<223> OTHER INFORMATION: Synthetic Construct

<400> SEQUENCE: 5

Gln Ile Gln Leu Val Gln Ser Gly Pro Glu Leu Arg Lys Pro Gly Glu
1               5                   10                  15

Thr Val Lys Ile Ser Cys Lys Ala Ser Gly Phe Pro Phe Thr Thr Asp
            20                  25                  30

Gly Met Ser Trp Val Lys Gln Ala Pro Gly Lys Gly Leu Lys Trp Met
        35                  40                  45

Gly Trp Ile Asn Thr Tyr Ser Gly Val Pro Thr Tyr Ala Asp Asp Phe
    50                  55                  60

Lys Gly Arg Val Ala Phe Ser Leu Glu Thr Ser Ala Ser Thr Ala Tyr
65                  70                  75                  80

Leu Gln Ile Lys Asn Leu Lys Asn Glu Asp Thr Ala Thr Tyr Phe Cys
                85                  90                  95

Ala Arg Phe Arg Arg Gly Asn Ala Leu Asp Asn Trp Gly Gln Gly Thr
            100                 105                 110

Ser Val Thr Val Ser Ser
        115


<210> SEQ ID NO 6
<211> LENGTH: 113
<212> TYPE: PRT
<213> ORGANISM: Artificial Sequence
<220> FEATURE:
<223> OTHER INFORMATION: Synthetic Construct

<400> SEQUENCE: 6

Asp Ile Val Met Thr Gln Ser Pro Ser Ser Leu Thr Val Thr Ala Gly
1               5                   10                  15
```

```
Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Ile Tyr Tyr Cys Gln Asn
                85                  90                  95

Asn Tyr Phe Tyr Pro Leu Thr Phe Gly Ala Gly Thr Arg Leu Glu Leu
            100                 105                 110

Lys


<210> SEQ ID NO 7
<211> LENGTH: 118
<212> TYPE: PRT
<213> ORGANISM: Artificial Sequence
<220> FEATURE:
<223> OTHER INFORMATION: Synthetic Construct

<400> SEQUENCE: 7

Glu Val Gln Leu Gln Gln Ser Gly Pro Glu Leu Glu Lys Pro Gly Ala
1               5                   10                  15

Ser Val Lys Ile Ser Cys Lys Ala Ser Gly Tyr Ser Phe Thr Gly Tyr
            20                  25                  30

Lys Met Asn Trp Val Lys Gln Ser Asn Gly Glu Ser Leu Glu Trp Ile
        35                  40                  45

Gly Asn Ile Asp Pro Tyr Tyr Gly Asp Thr Thr Tyr Thr Gln Lys Phe
    50                  55                  60

Lys Gly Lys Ala Thr Phe Thr Val Asp Thr Ser Ser Ser Thr Ala Tyr
65                  70                  75                  80

Met Gln Leu Lys Ser Leu Thr Ser Glu Asp Ser Ala Val Tyr Phe Cys
                85                  90                  95

Ala Arg Tyr Asn Arg Gly Asn Thr Met Asp Tyr Trp Gly Gln Gly Thr
            100                 105                 110

Ser Val Thr Val Ser Ser
        115


<210> SEQ ID NO 8
<211> LENGTH: 113
<212> TYPE: PRT
<213> ORGANISM: Artificial Sequence
<220> FEATURE:
<223> OTHER INFORMATION: Synthetic Construct

<400> SEQUENCE: 8

Asp Ile Val Met Thr Gln Ser Pro Ser Ser Leu Thr Val Thr Ala Gly
1               5                   10                  15

Glu Lys Val Thr Leu Ser Cys Lys Ser Ser Gln Ser Leu Leu Asn Ser
            20                  25                  30

Gly Asn Gln Lys Asn Tyr Leu Thr Trp Tyr Gln Gln Arg Pro Gly Gln
        35                  40                  45

Pro Pro Lys Leu Leu Ile Tyr Trp Ala Ser Thr Arg Glu Ser Gly Val
    50                  55                  60

Pro Val Arg Phe Thr Gly Ser Gly Ser Gly Ala Asp Phe Thr Leu Thr
65                  70                  75                  80
```

```
Ile Ser Ser Val Gln Ala Glu Asp Leu Ala Val Tyr Phe Cys Gln Asn
                85                  90                  95

Ala Tyr Phe Tyr Pro Leu Thr Phe Gly Thr Gly Thr Lys Leu Glu Leu
            100                 105                 110

Arg


<210> SEQ ID NO 9
<211> LENGTH: 330
<212> TYPE: PRT
<213> ORGANISM: Artificial Sequence
<220> FEATURE:
<223> OTHER INFORMATION: Synthetic Construct

<400> SEQUENCE: 9

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
```

325 330

<210> SEQ ID NO 10
<211> LENGTH: 107
<212> TYPE: PRT
<213> ORGANISM: Artificial Sequence
<220> FEATURE:
<223> OTHER INFORMATION: Synthetic Construct

<400> SEQUENCE: 10

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 11
<211> LENGTH: 8
<212> TYPE: PRT
<213> ORGANISM: Artificial Sequence
<220> FEATURE:
<223> OTHER INFORMATION: Synthetic Construct

<400> SEQUENCE: 11

```
Gly Tyr Ala Phe Thr Asn Tyr Leu
1               5
```

<210> SEQ ID NO 12
<211> LENGTH: 8
<212> TYPE: PRT
<213> ORGANISM: Artificial Sequence
<220> FEATURE:
<223> OTHER INFORMATION: Synthetic Construct

<400> SEQUENCE: 12

```
Ile Asn Pro Gly Ser Gly Gly Thr
1               5
```

<210> SEQ ID NO 13
<211> LENGTH: 11
<212> TYPE: PRT
<213> ORGANISM: Artificial Sequence
<220> FEATURE:
<223> OTHER INFORMATION: Synthetic Construct

<400> SEQUENCE: 13

```
Ala Arg Val Tyr Tyr Gly Asn Ser Phe Gly Tyr
1               5                   10
```

<210> SEQ ID NO 14
<211> LENGTH: 12
<212> TYPE: PRT
<213> ORGANISM: Artificial Sequence
<220> FEATURE:
<223> OTHER INFORMATION: Synthetic Construct

<400> SEQUENCE: 14

```
Gln Ser Leu Leu Asn Ser Gly Asn Gln Lys Asn Tyr
1               5                   10
```

<210> SEQ ID NO 15
<211> LENGTH: 3
<212> TYPE: PRT
<213> ORGANISM: Artificial Sequence
<220> FEATURE:
<223> OTHER INFORMATION: Synthetic Construct

<400> SEQUENCE: 15

```
Trp Ala Ser
1
```

<210> SEQ ID NO 16
<211> LENGTH: 9
<212> TYPE: PRT
<213> ORGANISM: Artificial Sequence
<220> FEATURE:
<223> OTHER INFORMATION: Synthetic Construct

<400> SEQUENCE: 16

```
Gln Asn Glu Tyr Phe Tyr Pro Phe Thr
1               5
```

<210> SEQ ID NO 17
<211> LENGTH: 8
<212> TYPE: PRT
<213> ORGANISM: Artificial Sequence
<220> FEATURE:
<223> OTHER INFORMATION: Synthetic Construct

<400> SEQUENCE: 17

```
Gly Tyr Ser Phe Thr Gly Tyr Lys
1               5
```

<210> SEQ ID NO 18
<211> LENGTH: 8
<212> TYPE: PRT
<213> ORGANISM: Artificial Sequence
<220> FEATURE:
<223> OTHER INFORMATION: Synthetic Construct

<400> SEQUENCE: 18

```
Ile Asp Pro Tyr Tyr Gly Gly Thr
1               5
```

<210> SEQ ID NO 19
<211> LENGTH: 11
<212> TYPE: PRT
<213> ORGANISM: Artificial Sequence
<220> FEATURE:
<223> OTHER INFORMATION: Synthetic Construct

<400> SEQUENCE: 19

```
Ala Arg Tyr Gly Lys Gly Asn Thr Met Asp Tyr
1               5                   10
```

<210> SEQ ID NO 20
<211> LENGTH: 12
<212> TYPE: PRT
<213> ORGANISM: Artificial Sequence
<220> FEATURE:
<223> OTHER INFORMATION: Synthetic Construct

<400> SEQUENCE: 20

Gln Ser Leu Leu Asn Ser Gly Asn Gln Lys Asn Tyr
1               5                   10

<210> SEQ ID NO 21
<211> LENGTH: 3
<212> TYPE: PRT
<213> ORGANISM: Artificial Sequence
<220> FEATURE:
<223> OTHER INFORMATION: Synthetic Construct

<400> SEQUENCE: 21

Trp Ala Ser
1

<210> SEQ ID NO 22
<211> LENGTH: 9
<212> TYPE: PRT
<213> ORGANISM: Artificial Sequence
<220> FEATURE:
<223> OTHER INFORMATION: Synthetic Construct

<400> SEQUENCE: 22

Gln Asn Ala Tyr Ile Tyr Pro Leu Thr
1               5

<210> SEQ ID NO 23
<211> LENGTH: 8
<212> TYPE: PRT
<213> ORGANISM: Artificial Sequence
<220> FEATURE:
<223> OTHER INFORMATION: Synthetic Construct

<400> SEQUENCE: 23

Gly Phe Pro Phe Thr Thr Asp Gly
1               5

<210> SEQ ID NO 24
<211> LENGTH: 8
<212> TYPE: PRT
<213> ORGANISM: Artificial Sequence
<220> FEATURE:
<223> OTHER INFORMATION: Synthetic Construct

<400> SEQUENCE: 24

Ile Asn Thr Tyr Ser Gly Val Pro
1               5

<210> SEQ ID NO 25
<211> LENGTH: 11
<212> TYPE: PRT
<213> ORGANISM: Artificial Sequence
<220> FEATURE:
<223> OTHER INFORMATION: Synthetic Construct

<400> SEQUENCE: 25

Ala Arg Phe Arg Arg Gly Asn Ala Leu Asp Asn
1               5                   10

<210> SEQ ID NO 26
<211> LENGTH: 12
<212> TYPE: PRT
<213> ORGANISM: Artificial Sequence
<220> FEATURE:
<223> OTHER INFORMATION: Synthetic Construct

<400> SEQUENCE: 26

```
Gln Ser Leu Leu Asn Ser Gly Asn Gln Lys Asn Tyr
1               5                   10


<210> SEQ ID NO 27
<211> LENGTH: 3
<212> TYPE: PRT
<213> ORGANISM: Artificial Sequence
<220> FEATURE:
<223> OTHER INFORMATION: Synthetic Construct

<400> SEQUENCE: 27

Trp Ala Ser
1


<210> SEQ ID NO 28
<211> LENGTH: 9
<212> TYPE: PRT
<213> ORGANISM: Artificial Sequence
<220> FEATURE:
<223> OTHER INFORMATION: Synthetic Construct

<400> SEQUENCE: 28

Gln Asn Asn Tyr Phe Tyr Pro Leu Thr
1               5


<210> SEQ ID NO 29
<211> LENGTH: 8
<212> TYPE: PRT
<213> ORGANISM: Artificial Sequence
<220> FEATURE:
<223> OTHER INFORMATION: Synthetic Construct

<400> SEQUENCE: 29

Gly Tyr Ser Phe Thr Gly Tyr Lys
1               5


<210> SEQ ID NO 30
<211> LENGTH: 8
<212> TYPE: PRT
<213> ORGANISM: Artificial Sequence
<220> FEATURE:
<223> OTHER INFORMATION: Synthetic Construct

<400> SEQUENCE: 30

Ile Asp Pro Tyr Tyr Gly Asp Thr
1               5


<210> SEQ ID NO 31
<211> LENGTH: 11
<212> TYPE: PRT
<213> ORGANISM: Artificial Sequence
<220> FEATURE:
<223> OTHER INFORMATION: Synthetic Construct

<400> SEQUENCE: 31

Ala Arg Tyr Asn Arg Gly Asn Thr Met Asp Tyr
1               5                   10


<210> SEQ ID NO 32
<211> LENGTH: 12
<212> TYPE: PRT
<213> ORGANISM: Artificial Sequence
<220> FEATURE:
<223> OTHER INFORMATION: Synthetic Construct

<400> SEQUENCE: 32
```

```
Gln Ser Leu Leu Asn Ser Gly Asn Gln Lys Asn Tyr
1               5                   10


<210> SEQ ID NO 33
<211> LENGTH: 3
<212> TYPE: PRT
<213> ORGANISM: Artificial Sequence
<220> FEATURE:
<223> OTHER INFORMATION: Synthetic Construct

<400> SEQUENCE: 33

Trp Ala Ser
1


<210> SEQ ID NO 34
<211> LENGTH: 9
<212> TYPE: PRT
<213> ORGANISM: Artificial Sequence
<220> FEATURE:
<223> OTHER INFORMATION: Synthetic Construct

<400> SEQUENCE: 34

Gln Asn Ala Tyr Phe Tyr Pro Leu Thr
1               5


<210> SEQ ID NO 35
<211> LENGTH: 43
<212> TYPE: DNA
<213> ORGANISM: Artificial Sequence
<220> FEATURE:
<223> OTHER INFORMATION: Synthetic Construct

<400> SEQUENCE: 35

gattacgcca agctttcatt taccaggaga gtgggagagg ctc                        43


<210> SEQ ID NO 36
<211> LENGTH: 43
<212> TYPE: DNA
<213> ORGANISM: Artificial Sequence
<220> FEATURE:
<223> OTHER INFORMATION: Synthetic Construct

<400> SEQUENCE: 36

gattacgcca agctttcatt tacccggagt ccgggagaag ctc                        43


<210> SEQ ID NO 37
<211> LENGTH: 43
<212> TYPE: DNA
<213> ORGANISM: Artificial Sequence
<220> FEATURE:
<223> OTHER INFORMATION: Synthetic Construct

<400> SEQUENCE: 37

gattacgcca agctttcaac actcattcct gttgaagctc ttg                        43


<210> SEQ ID NO 38
<211> LENGTH: 261
<212> TYPE: PRT
<213> ORGANISM: Artificial Sequence
<220> FEATURE:
<223> OTHER INFORMATION: Synthetic Construct

<400> SEQUENCE: 38

Met Ala Val Thr Ala Cys Gln Gly Leu Gly Phe Val Val Ser Leu Ile
1               5                   10                  15

Gly Ile Ala Gly Ile Ile Ala Ala Thr Cys Met Asp Gln Trp Ser Thr
```

```
            20                  25                  30

Gln Asp Leu Tyr Asn Asn Pro Val Thr Ala Val Phe Asn Tyr Gln Gly
        35                  40                  45

Leu Trp Arg Ser Cys Val Arg Glu Ser Ser Gly Phe Thr Glu Cys Arg
    50                  55                  60

Gly Tyr Phe Thr Leu Leu Gly Leu Pro Ala Met Leu Gln Ala Val Arg
65                  70                  75                  80

Ala Leu Met Ile Val Gly Ile Val Leu Gly Ala Ile Gly Leu Leu Val
                85                  90                  95

Ser Ile Phe Ala Leu Lys Cys Ile Arg Ile Gly Ser Met Glu Asp Ser
            100                 105                 110

Ala Lys Ala Asn Met Thr Leu Thr Ser Gly Ile Met Phe Ile Val Ser
        115                 120                 125

Gly Leu Cys Ala Ile Ala Gly Val Ser Val Phe Ala Asn Met Leu Val
    130                 135                 140

Thr Asn Phe Trp Met Ser Thr Ala Asn Met Tyr Thr Gly Met Gly Gly
145                 150                 155                 160

Met Val Gln Thr Val Gln Thr Arg Tyr Thr Phe Gly Ala Ala Leu Phe
                165                 170                 175

Val Gly Trp Val Ala Gly Gly Leu Thr Leu Ile Gly Gly Val Met Met
            180                 185                 190

Cys Ile Ala Cys Arg Gly Leu Ala Pro Glu Glu Thr Asn Tyr Lys Ala
        195                 200                 205

Val Ser Tyr His Ala Ser Gly His Ser Val Ala Tyr Lys Pro Gly Gly
    210                 215                 220

Phe Lys Ala Ser Thr Gly Phe Gly Ser Asn Thr Lys Asn Lys Lys Ile
225                 230                 235                 240

Tyr Asp Gly Gly Ala Arg Thr Glu Asp Glu Val Gln Ser Tyr Pro Ser
                245                 250                 255

Lys His Asp Tyr Val
            260


<210> SEQ ID NO 39
<211> LENGTH: 261
<212> TYPE: PRT
<213> ORGANISM: Artificial Sequence
<220> FEATURE:
<223> OTHER INFORMATION: Synthetic Construct

<400> SEQUENCE: 39

Met Ser Thr Thr Thr Cys Gln Val Val Ala Phe Leu Leu Ser Ile Leu
1               5                   10                  15

Gly Leu Ala Gly Cys Ile Ala Ala Thr Gly Met Asp Met Trp Ser Thr
            20                  25                  30

Gln Asp Leu Tyr Asp Asn Pro Val Thr Ser Val Phe Gln Tyr Glu Gly
        35                  40                  45

Leu Trp Arg Ser Cys Val Arg Gln Ser Ser Gly Phe Thr Glu Cys Arg
    50                  55                  60

Pro Tyr Phe Thr Ile Leu Gly Leu Pro Ala Met Leu Gln Ala Val Arg
65                  70                  75                  80

Ala Leu Met Ile Val Gly Ile Val Leu Gly Ala Ile Gly Leu Leu Val
                85                  90                  95

Ser Ile Phe Ala Leu Lys Cys Ile Arg Ile Gly Ser Met Glu Asp Ser
            100                 105                 110

Ala Lys Ala Asn Met Thr Leu Thr Ser Gly Ile Met Phe Ile Val Ser
```

```
        115                 120                 125

Gly Leu Cys Ala Ile Ala Gly Val Ser Val Phe Ala Asn Met Leu Val
    130                 135                 140

Thr Asn Phe Trp Met Ser Thr Ala Asn Met Tyr Thr Gly Met Gly Gly
145                 150                 155                 160

Met Val Gln Thr Val Gln Thr Arg Tyr Thr Phe Gly Ala Ala Leu Phe
                165                 170                 175

Val Gly Trp Val Ala Gly Gly Leu Thr Leu Ile Gly Gly Val Met Met
            180                 185                 190

Cys Ile Ala Cys Arg Gly Leu Ala Pro Glu Glu Thr Asn Tyr Lys Ala
        195                 200                 205

Val Ser Tyr His Ala Ser Gly His Ser Val Ala Tyr Lys Pro Gly Gly
    210                 215                 220

Phe Lys Ala Ser Thr Gly Phe Gly Ser Asn Thr Lys Asn Lys Lys Ile
225                 230                 235                 240

Tyr Asp Gly Gly Ala Arg Thr Glu Asp Glu Val Gln Ser Tyr Pro Ser
                245                 250                 255

Lys His Asp Tyr Val
            260


<210> SEQ ID NO 40
<211> LENGTH: 330
<212> TYPE: PRT
<213> ORGANISM: Artificial Sequence
<220> FEATURE:
<223> OTHER INFORMATION: Synthetic Construct

<400> SEQUENCE: 40

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Val Gly Gly Pro Ser Val Phe Leu Leu Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Pro Glu
                165                 170                 175

Glu Gln Tyr Asn Ser Thr Leu Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
```

```
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Leu Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 41
<211> LENGTH: 5
<212> TYPE: PRT
<213> ORGANISM: Artificial Sequence
<220> FEATURE:
<223> OTHER INFORMATION: Synthetic Construct

<400> SEQUENCE: 41

Gly Tyr Lys Met Asn
1               5


<210> SEQ ID NO 42
<211> LENGTH: 17
<212> TYPE: PRT
<213> ORGANISM: Artificial Sequence
<220> FEATURE:
<223> OTHER INFORMATION: Synthetic Construct

<400> SEQUENCE: 42

Asn Ile Asp Pro Tyr Tyr Gly Asp Thr Thr Tyr Thr Gln Lys Phe Lys
1               5                   10                  15

Gly


<210> SEQ ID NO 43
<211> LENGTH: 9
<212> TYPE: PRT
<213> ORGANISM: Artificial Sequence
<220> FEATURE:
<223> OTHER INFORMATION: Synthetic Construct

<400> SEQUENCE: 43

Tyr Asn Arg Gly Asn Thr Met Asp Tyr
1               5


<210> SEQ ID NO 44
<211> LENGTH: 17
<212> TYPE: PRT
<213> ORGANISM: Artificial Sequence
<220> FEATURE:
<223> OTHER INFORMATION: Synthetic Construct

<400> SEQUENCE: 44

Lys Ser Ser Gln Ser Leu Leu Asn Ser Gly Asn Gln Lys Asn Tyr Leu
1               5                   10                  15

Thr
```

<210> SEQ ID NO 45
<211> LENGTH: 7
<212> TYPE: PRT
<213> ORGANISM: Artificial Sequence
<220> FEATURE:
<223> OTHER INFORMATION: Synthetic Construct

<400> SEQUENCE: 45

Trp Ala Ser Thr Arg Glu Ser
1 5

<210> SEQ ID NO 46
<211> LENGTH: 9
<212> TYPE: PRT
<213> ORGANISM: Artificial Sequence
<220> FEATURE:
<223> OTHER INFORMATION: Synthetic Construct

<400> SEQUENCE: 46

Gln Asn Ala Tyr Phe Tyr Pro Leu Thr
1 5

<210> SEQ ID NO 47
<211> LENGTH: 7
<212> TYPE: PRT
<213> ORGANISM: Artificial Sequence
<220> FEATURE:
<223> OTHER INFORMATION: Synthetic Construct

<400> SEQUENCE: 47

Gly Tyr Ser Phe Thr Gly Tyr
1 5

<210> SEQ ID NO 48
<211> LENGTH: 6
<212> TYPE: PRT
<213> ORGANISM: Artificial Sequence
<220> FEATURE:
<223> OTHER INFORMATION: Synthetic Construct

<400> SEQUENCE: 48

Asp Pro Tyr Tyr Gly Asp
1 5

<210> SEQ ID NO 49
<211> LENGTH: 9
<212> TYPE: PRT
<213> ORGANISM: Artificial Sequence
<220> FEATURE:
<223> OTHER INFORMATION: Synthetic Construct

<400> SEQUENCE: 49

Tyr Asn Arg Gly Asn Thr Met Asp Tyr
1 5

<210> SEQ ID NO 50
<211> LENGTH: 17
<212> TYPE: PRT
<213> ORGANISM: Artificial Sequence
<220> FEATURE:
<223> OTHER INFORMATION: Synthetic Construct

<400> SEQUENCE: 50

Lys Ser Ser Gln Ser Leu Leu Asn Ser Gly Asn Gln Lys Asn Tyr Leu
1 5 10 15

Thr

<210> SEQ ID NO 51
<211> LENGTH: 7
<212> TYPE: PRT
<213> ORGANISM: Artificial Sequence
<220> FEATURE:
<223> OTHER INFORMATION: Synthetic Construct

<400> SEQUENCE: 51

```
Trp Ala Ser Thr Arg Glu Ser
1               5
```

<210> SEQ ID NO 52
<211> LENGTH: 9
<212> TYPE: PRT
<213> ORGANISM: Artificial Sequence
<220> FEATURE:
<223> OTHER INFORMATION: Synthetic Construct

<400> SEQUENCE: 52

```
Gln Asn Ala Tyr Phe Tyr Pro Leu Thr
1               5
```

<210> SEQ ID NO 53
<211> LENGTH: 6
<212> TYPE: PRT
<213> ORGANISM: Artificial Sequence
<220> FEATURE:
<223> OTHER INFORMATION: Synthetic Construct

<400> SEQUENCE: 53

```
Thr Gly Tyr Lys Met Asn
1               5
```

<210> SEQ ID NO 54
<211> LENGTH: 13
<212> TYPE: PRT
<213> ORGANISM: Artificial Sequence
<220> FEATURE:
<223> OTHER INFORMATION: Synthetic Construct

<400> SEQUENCE: 54

```
Trp Ile Gly Asn Ile Asp Pro Tyr Tyr Gly Asp Thr Thr
1               5                   10
```

<210> SEQ ID NO 55
<211> LENGTH: 10
<212> TYPE: PRT
<213> ORGANISM: Artificial Sequence
<220> FEATURE:
<223> OTHER INFORMATION: Synthetic Construct

<400> SEQUENCE: 55

```
Ala Arg Tyr Asn Arg Gly Asn Thr Met Asp
1               5                   10
```

<210> SEQ ID NO 56
<211> LENGTH: 13
<212> TYPE: PRT
<213> ORGANISM: Artificial Sequence
<220> FEATURE:
<223> OTHER INFORMATION: Synthetic Construct

<400> SEQUENCE: 56

```
Leu Asn Ser Gly Asn Gln Lys Asn Tyr Leu Thr Trp Tyr
1               5                   10
```

-continued

```
<210> SEQ ID NO 57
<211> LENGTH: 10
<212> TYPE: PRT
<213> ORGANISM: Artificial Sequence
<220> FEATURE:
<223> OTHER INFORMATION: Synthetic Construct

<400> SEQUENCE: 57

Leu Leu Ile Tyr Trp Ala Ser Thr Arg Glu
1               5                   10


<210> SEQ ID NO 58
<211> LENGTH: 8
<212> TYPE: PRT
<213> ORGANISM: Artificial Sequence
<220> FEATURE:
<223> OTHER INFORMATION: Synthetic Construct

<400> SEQUENCE: 58

Gln Asn Ala Tyr Phe Tyr Pro Leu
1               5
```

MONOCLONAL ANTIBODIES AGAINST CLDN18.2 AND Fc-ENGINEERED VERSIONS THEREOF

CROSS-REFERENCE TO RELATED APPLICATIONS

This application is a Section 371 of International Patent Application No. PCT/CN2022/095841, filed on May 30, 2022, which published in the English language on Dec. 8, 2022, under International Publication No. WO 2022/253156 A1, which claims priority to PCT Patent Application Nos. PCT/CN2021/097239 and PCT/CN2021/097240, filed on May 31, 2021, and PCT Patent Application Nos. PCT/CN2021/106783 and PCT/CN2021/106784, filed on Jul. 16, 2021. Each disclosure is incorporated by reference in its entirety.

REFERENCE TO SEQUENCE LISTING SUBMITTED ELECTRONICALLY

This application contains a sequence listing, which is submitted electronically via EFS-Web as an ASCII formatted sequence listing with a file name "065824.29US1 Sequence Listing" and a creation date of Nov. 29, 2023, and having a size of 28.9 kb. The sequence listing submitted via EFS-Web is part of the specification and is herein incorporated by reference in its entirety.

FIELD OF THE INVENTION

A panel of monoclonal antibodies which specifically bind to CLDN18.2 and do not specifically bind to CLDN18.1, and optionally have an engineered Fc region is provided.

BACKGROUND

The tight junction molecule Claudin 18 splice variant 2 (Claudin 18.2, CLDN18.2) is a member of the claudin family of tight junction proteins. CLDN18.2 is a 27.8 kDa transmembrane protein comprising four membrane spanning domains with two small extracellular loops.

In normal tissues there is no detectable expression of CLDN18.2 by RT-PCR with exception of stomach. Immunohistochemistry with CLDN18.2 specific antibodies reveals stomach as the only positive tissue.

CLDN18.2 is a highly selective gastric lineage antigen expressed exclusively on short-lived differentiated gastric epithelial cells. CLDN18.2 is maintained in the course of malignant transformation and thus frequently displayed on the surface of human gastric cancer cells. Moreover, this pan-tumoral antigen is ectopically activated at significant levels in esophageal, pancreatic and lung adenocarcinomas. The CLDN18.2 protein is also localized in lymph node metastases of gastric cancer adenocarcinomas and in distant metastases especially into the ovary (so-called Krukenberg tumors).

SUMMARY

The invention provides anti-CLDN18.2 antibodies.

The invention provides an isolated monoclonal antibody, particularly Fc-engineered, that specifically binds to human CLDN18.2, wherein the antibody comprises (1) a HVR-H1, a HVR-H2 and a HVR-H3 comprised in a VH as set forth in SEQ ID NO: 1, and a HVR-L1, a HVR-L2 and a HVR-L3 comprised in a VL as set forth in SEQ ID NO: 2;

(2) a HVR-H1, a HVR-H2 and a HVR-H3 comprised in a VH as set forth in SEQ ID NO: 3, and a HVR-L1, a HVR-L2 and a HVR-L3 comprised in a VL as set forth in SEQ ID NO: 4;

(3) a HVR-H1, a HVR-H2 and a HVR-H3 comprised in a VH as set forth in SEQ ID NO: 5, and a HVR-L1, a HVR-L2 and a HVR-L3 comprised in a VL as set forth in SEQ ID NO: 6; or (4) a HVR-H1, a HVR-H2 and a HVR-H3 comprised in a VH as set forth in SEQ ID NO: 7, and a HVR-L1, a HVR-L2 and a HVR-L3 comprised in a VL as set forth in SEQ ID NO: 8, e.g., as shown in FIG. 1A, 1B, 1C or 1D, and optionally, comprises one or more mutations in the Fc region.

In one embodiment, the antibody comprises (1) a HVR-H1 as set forth in SEQ ID NO: 11, a HVR-H2 as set forth in SEQ ID NO: 12, a HVR-H3 as set forth in SEQ ID NO: 13, a HVR-L1 as set forth in SEQ ID NO: 14, a HVR-L2 as set forth in SEQ ID NO: 15, and a HVR-L3 as set forth in SEQ ID NO: 16;

(2) a HVR-H1 as set forth in SEQ ID NO: 17, a HVR-H2 as set forth in SEQ ID NO: 18, a HVR-H3 as set forth in SEQ ID NO: 19, a HVR-L1 as set forth in SEQ ID NO: 20, a HVR-L2 as set forth in SEQ ID NO: 21, and a HVR-L3 as set forth in SEQ ID NO: 22;

(3) a HVR-H1 as set forth in SEQ ID NO: 23, a HVR-H2 as set forth in SEQ ID NO: 24, a HVR-H3 as set forth in SEQ ID NO: 25, a HVR-L1 as set forth in SEQ ID NO: 26, a HVR-L2 as set forth in SEQ ID NO: 27, and a HVR-L3 as set forth in SEQ ID NO: 28; or (4) a HVR-H1 as set forth in SEQ ID NO: 29, a HVR-H2 as set forth in SEQ ID NO: 30, a HVR-H3 as set forth in SEQ ID NO: 31, a HVR-L1 as set forth in SEQ ID NO: 32, a HVR-L2 as set forth in SEQ ID NO: 33, and a HVR-L3 as set forth in SEQ ID NO: 34.

In one embodiment, the antibody comprises (1) a HVR-H1 as set forth in SEQ ID NO: 41, a HVR-H2 as set forth in SEQ ID NO: 42, a HVR-H3 as set forth in SEQ ID NO: 43, a HVR-L1 as set forth in SEQ ID NO: 44, a HVR-L2 as set forth in SEQ ID NO: 45, and a HVR-L3 as set forth in SEQ ID NO: 46;

(2) a HVR-H1 as set forth in SEQ ID NO: 47, a HVR-H2 as set forth in SEQ ID NO: 48, a HVR-H3 as set forth in SEQ ID NO: 49, a HVR-L1 as set forth in SEQ ID NO: 50, a HVR-L2 as set forth in SEQ ID NO: 51, and a HVR-L3 as set forth in SEQ ID NO: 52; or (3) a HVR-H1 as set forth in SEQ ID NO: 53, a HVR-H2 as set forth in SEQ ID NO: 54, a HVR-H3 as set forth in SEQ ID NO: 55, a HVR-L1 as set forth in SEQ ID NO: 56, a HVR-L2 as set forth in SEQ ID NO: 57, and a HVR-L3 as set forth in SEQ ID NO: 58.

The invention further provides an isolated monoclonal antibody, particularly Fc-engineered, that specifically binds to human CLDN18.2, wherein the antibody comprises (1) a VH comprising a HVR-H1 as set forth in SEQ ID NO: 11, a HVR-H2 as set forth in SEQ ID NO: 12 and a HVR-H3 as set forth in SEQ ID NO: 13, and a VL comprising a HVR-L1 as set forth in SEQ ID NO: 14, a HVR-L2 as set forth in SEQ ID NO: 15 and a HVR-L3 as set forth in SEQ ID NO: 16;

(2) a VH comprising a HVR-H1 as set forth in SEQ ID NO: 17, a HVR-H2 as set forth in SEQ ID NO: 18 and a HVR-H3 as set forth in SEQ ID NO: 19, and a VL comprising a HVR-L1 as set forth in SEQ ID NO: 20, a HVR-L2 as set forth in SEQ ID NO: 21 and a HVR-L3 as set forth in SEQ ID NO: 22;

(3) a VH comprising a HVR-H1 as set forth in SEQ ID NO: 23, a HVR-H2 as set forth in SEQ ID NO: 24 and a HVR-H3 as set forth in SEQ ID NO: 25, and a VL comprising a HVR-L1 as set forth in SEQ ID NO: 26, a HVR-L2 as set forth in SEQ ID NO: 27 and a HVR-L3 as set forth in SEQ ID NO: 28; or (4) a VH comprising a HVR-H1 as set forth in SEQ ID NO: 29, a HVR-H2 as set forth in SEQ ID NO: 30 and a HVR-H3 as set forth in SEQ ID NO: 31, and a VL comprising a HVR-L1 as set forth in SEQ ID NO: 32, a HVR-L2 as set forth in SEQ ID NO: 33 and a HVR-L3 as set forth in SEQ ID NO: 34, and optionally, comprises one or more mutations in the Fc region.

The invention further provides an isolated monoclonal antibody, particularly Fc-engineered, that specifically binds to human CLDN18.2, wherein the antibody comprises (1) a VH comprising a HVR-H1 as set forth in SEQ ID NO: 41, a HVR-H2 as set forth in SEQ ID NO: 42 and a HVR-H3 as set forth in SEQ ID NO: 43, and a VL comprising a HVR-L1 as set forth in SEQ ID NO: 44, a HVR-L2 as set forth in SEQ ID NO: 45 and a HVR-L3 as set forth in SEQ ID NO: 46;

(2) a VH comprising a HVR-H1 as set forth in SEQ ID NO: 47, a HVR-H2 as set forth in SEQ ID NO: 48 and a HVR-H3 as set forth in SEQ ID NO: 49, and a VL comprising a HVR-L1 as set forth in SEQ ID NO: 50, a HVR-L2 as set forth in SEQ ID NO: 51 and a HVR-L3 as set forth in SEQ ID NO: 52; or (3) a VH comprising a HVR-H1 as set forth in SEQ ID NO: 53, a HVR-H2 as set forth in SEQ ID NO: 54 and a HVR-H3 as set forth in SEQ ID NO: 55, and a VL comprising a HVR-L1 as set forth in SEQ ID NO: 56, a HVR-L2 as set forth in SEQ ID NO: 57 and a HVR-L3 as set forth in SEQ ID NO: 58, and optionally, comprises one or more mutations in the Fc region.

The invention further provides an isolated monoclonal antibody, particularly Fc-engineered, that specifically binds to human CLDN18.2, wherein the antibody comprises (1) a VH as set forth in SEQ ID NO: 1 and a VL as set forth in SEQ ID NO: 2;

(2) a VH as set forth in SEQ ID NO: 3 and a VL as set forth in SEQ ID NO: 4;

(3) a VH as set forth in SEQ ID NO: 5 and a VL as set forth in SEQ ID NO: 6; or (4) a VH as set forth in SEQ ID NO: 7 and a VL as set forth in SEQ ID NO: 8, and optionally, comprises one or more mutations in the Fc region, optionally, wherein the first two N-terminal amino acid residues of the VH are absent.

In one embodiment, the one or more mutations in the Fc region are one or more mutations that modify, e.g., increase or decrease, binding to an Fc receptor and/or effector function, e.g., ADCC and/or CDC. In one embodiment, the one or more mutations in the Fc region are one or more substitutions selected from the group consisting of L235V, F243L, R292P, Y300L and P396L. In one embodiment, the one or more mutations in the Fc region are L235V, F243L, R292P, Y300L and P396L.

The invention further provides isolated monoclonal antibody, particularly Fc-engineered, that specifically binds to human CLDN18.2, wherein the antibody:

i) competes for binding to human CLDN18.2 with an anti-CLDN18.2 antibody comprising (1) a VH as set forth in SEQ ID NO: 1 and a VL as set forth in SEQ ID NO: 2; (2) a VH as set forth in SEQ ID NO: 3 and a VL as set forth in SEQ ID NO: 4; (3) a VH as set forth in SEQ ID NO: 5 and a VL as set forth in SEQ ID NO: 6; or (4) a VH as set forth in SEQ ID NO: 7 and a VL as set forth in SEQ ID NO: 8, and/or ii) binds to the same epitope on human CLDN18.2 as an anti-CLDN18.2 antibody comprising (1) a VH as set forth in SEQ ID NO: 1 and a VL as set forth in SEQ ID NO: 2; (2) a VH as set forth in SEQ ID NO: 3 and a VL as set forth in SEQ ID NO: 4; (3) a VH as set forth in SEQ ID NO: 5 and a VL as set forth in SEQ ID NO: 6; or (4) a VH as set forth in SEQ ID NO: 7 and a VL as set forth in SEQ ID NO: 8; and/or iii) mediates ADCC of PBMC on cells (e.g., 293T cells or CHO cells or CT26 cells or KATOIII cells or NCI-N87 cells) that express human CLDN18.2, e.g., with an EC50 value at, around or less than 10 nM, 9 nM, 8 nM, 7 nM, 6 nM, 5 nM, 4 nM, 3 nM, 2 nM, 1 nM, 0.9 nM, 0.8 nM, 0.7 nM, 0.6 nM, 0.5 nM, 0.4 nM, 0.3 nM, 0.2 nM, 0.1 nM, 0.09 nM, 0.08 nM, 0.07 nM, 0.06 nM, 0.05 nM, 0.04 nM, 0.03 nM, 0.02 nM, 0.01 nM, 0.009 nM, 0.008 nM, 0.007 nM, 0.006 nM, 0.005 nM, 0.004 nM, 0.003 nM, 0.002 nM, or 0.001 nM, e.g., determined via LDH or FACS; and/or iv) does not mediates ADCC of PBMC on cells (e.g., 293T cells or CHO cells or CT26 cells or KATOIII cells or NCI-N87 cells) that express human CLDN18.1; and/or v) mediates CDC on cells (e.g., 293T cells or CHO cells or CT26 cells or KATOIII cells or NCI-N87 cells) that express human CLDN18.2, e.g., with an EC50 value at, around or less than 10 nM, 9 nM, 8 nM, 7 nM, 6 nM, 5 nM, 4 nM, 3 nM, 2 nM, 1 nM, 0.9 nM, 0.8 nM, 0.7 nM, 0.6 nM, 0.5 nM, 0.4 nM, 0.3 nM, 0.2 nM, 0.1 nM, 0.09 nM, 0.08 nM, 0.07 nM, 0.06 nM, 0.05 nM, 0.04 nM, 0.03 nM, 0.02 nM, 0.01 nM, 0.009 nM, 0.008 nM, 0.007 nM, 0.006 nM, 0.005 nM, 0.004 nM, 0.003 nM, 0.002 nM, or 0.001 nM, e.g., determined via LDH or FACS; and/or vi) does not mediates CDC on cells (e.g., 293T cells or CHO cells or CT26 cells or KATOIII cells or NCI-N87 cells) that express human CLDN18.1; and/or vii) binds to cells (e.g., 293T cells or CHO cells) that express human CLDN18.2 on the cell surface, e.g., with a Kd value at, around or less than 50 pM, 45 pM, 40 pM, 38.6 pM, 35 pM, 30 pM, 25 pM, 20 pM, 15 pM, 13.1 pM, 10 pM, 9.5 pM, 9 pM, or 5 pM; and/or viii) does not bind to cells (e.g., 293T cells or CHO cells) that express human CLDN18.1 on the cell surface; and/or ix) specifically binds to human CLDN18.2, e.g., with a Kd value at, around or less than 10 nM, 9.5 nM, 9 nM, 8.5 nM, 8 nM, 7.5 nM, 7 nM, 6.5 nM, 6.4 nM, 6 nM, 5.5 nM, 5 nM, 4.5 nM, 4 nM, 3.8 nM, 3.5 nM, 3 nM, 2.5 nM, 2 nM, 1.7 nM 1.5 nM, or 1 nM; and/or x) does not specifically bind to human CLDN18.1.

In one embodiment, the anti-CLDN18.2 monoclonal antibody according to the invention is a murine, chimeric, or humanized antibody.

In one embodiment, the anti-CLDN18.2 monoclonal antibody according to the invention is an antigen-binding antibody fragment, optionally selected from the group consisting of a Fab fragment, a Fab' fragment, a $F(ab')_2$ fragment, a scFv fragment, and a diabody.

In one embodiment, the anti-CLDN18.2 monoclonal antibody according to the invention is a full length antibody. In one embodiment, the anti-CLDN18.2 monoclonal antibody according to the invention comprises a human IgG, particularly IgG1, heavy chain constant region, optionally as set forth in SEQ ID NO: 9. In one embodiment, the anti-CLDN18.2 monoclonal antibody according to the invention comprises a mutated human IgG, particularly IgG1, heavy chain constant region, optionally as set forth in SEQ ID NO: 40. In one embodiment, the anti-CLDN18.2 monoclonal antibody according to the invention comprises a human kappa light chain constant region, optionally as set forth in SEQ ID NO: 10. In one embodiment, the anti-CLDN18.2 monoclonal antibody according to the invention is a chimeric antibody, e.g., a murine/human chimeric antibody. In one embodiment, the anti-CLDN18.2 monoclonal antibody according to the invention is Fc-engineered.

In one embodiment, the monoclonal antibody (mAb) or Fab fragment of the present invention has a crossover format (x-mAb or x-Fab), wherein either the variable domains or the (first) constant domains of the light and heavy chains are exchanged.

The invention provides an isolated nucleic acid encoding the monoclonal antibody of the invention. The invention provides a vector, e.g., a cloning vector or an expression vector, comprising the nucleic acid of the present invention. The invention provides a host cell comprising the nucleic acid of the present invention or the vector of the present invention. The invention provides a method of producing the monoclonal antibody of the invention comprising culturing the host cell so that the antibody is produced. In one embodiment, the method further comprises recovering the antibody from the host cell or the cell culture.

The invention provides a composition comprising the monoclonal antibody of the present invention. The invention provides a pharmaceutical formulation comprising the monoclonal antibody of the present invention and a pharmaceutically acceptable carrier.

The invention provides the monoclonal antibody of the invention for use as a medicament. The invention provides the monoclonal antibody of the invention for use in treating cancer. The invention provides the use of the monoclonal antibody of the invention in the manufacture of a medicament. In one embodiment, the medicament is for treatment of cancer. The invention provides a method of treating an individual having cancer comprising administering to the individual an effective amount of the monoclonal antibody of the invention.

BRIEF DESCRIPTION OF THE FIGURES

FIG. 1A shows the alignment of the amino acid sequences of VH and VL of the antibodies of the present invention, wherein the HVR sequences according to Kabat are highlighted by shade.

FIG. 1B shows the alignment of the amino acid sequences of VH and VL of the antibodies of the present invention, wherein the HVR sequences according to IMGT are highlighted by shade.

FIG. 1C shows the alignment of the amino acid sequences of VH and VL of the antibodies of the present invention, wherein the HVR sequences according to Chothia are highlighted by shade.

FIG. 1D shows the alignment of the amino acid sequences of VH and VL of the antibodies of the present invention, wherein the HVR sequences according to Contact are highlighted by shade.

FIG. 2 shows the binding of the antibodies of the present invention to CLDN18.2-expressing cells.

FIG. 3 shows the binding of the antibodies of the present invention to CLDN18.1-expressing cells.

FIG. 11 shows the CDC effect on CT26 expressing CLDN18.2 mediated by the antibodies of the present invention determined by LDH assay.

FIG. 12 shows the CDC effect on KATOIII expressing CLDN18.2 mediated by the antibodies of the present invention determined by LDH assay.

FIG. 13 shows the ADCC effect on KATOIII expressing CLDN18.2 mediated by the antibodies of the present invention determined by LDH assay.

FIG. 14 shows the ADCC effect on NCI-N87 expressing CLDN18.2 mediated by the antibodies of the present invention determined by LDH assay.

DETAILED DESCRIPTION OF THE INVENTION

I. Definition

Figure 4:
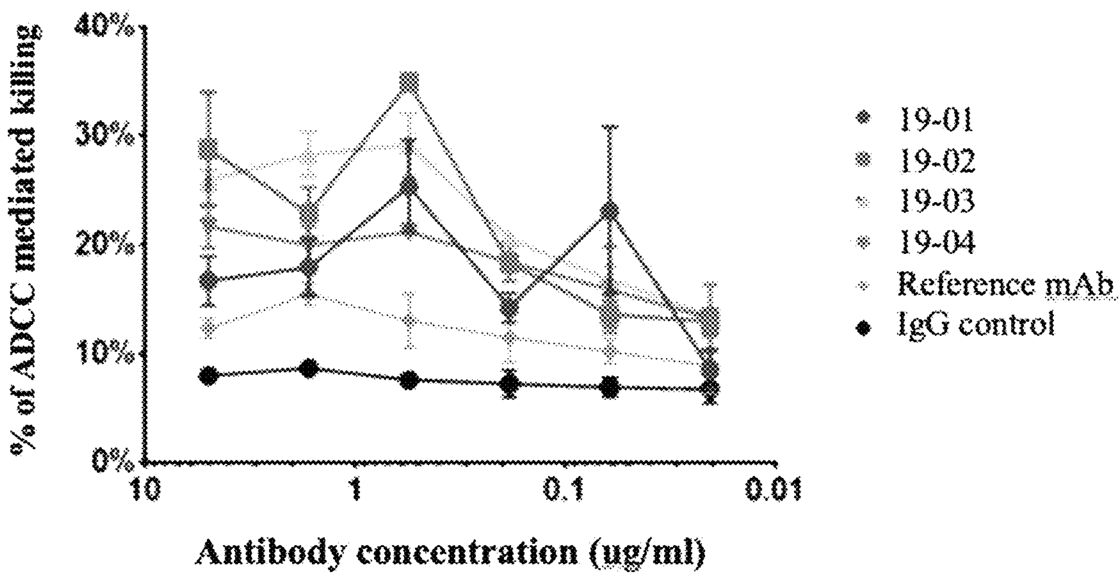
FIG. 4 shows the ADCC on CLDN18.2-expressing cells mediated by the antibodies of the present invention.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, $F(ab')_2$; diabodies; linear antibodies; single-chain antibody molecules (e.g. scFv); and multispecific antibodies formed from antibody fragments.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called $\alpha$, $\delta$, $\varepsilon$, $\gamma$, and $\mu$, respectively. The light chain can be assigned to one of two clearly distinct types, called kappa and lambda, based on the amino acid sequences of their constant domains.

"Effector functions" refer to those biological activities attributable to the Fc region of an antibody, which vary with the antibody isotype. Examples of antibody effector functions include: Clq binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

As used herein, the terms "engineer, engineered, engineering", are considered to include any manipulation of the peptide backbone or the post-translational modifications of a naturally occurring or recombinant polypeptide or fragment thereof. Engineering includes modifications of the amino acid sequence, of the glycosylation pattern, or of the side chain group of individual amino acids, as well as combinations of these approaches.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. In one embodiment the anti-CLDN18.2 antibody as described herein is of IgG1 isotype and comprises a heavy chain constant region of SEQ ID NO: 9 or of SEQ ID NO: 40. In one embodiment it comprises additionally the C-terminal lysine (Lys447). Unless otherwise specified herein, numbering of amino acid residues in the Fc region or constant region is according to the EU numbering system, also called the EU index, as described in Kabat et al., *Sequences of Proteins of Immunological Interest,* 5th Ed. Public Health Service, National Institutes of Health, Bethesda, MD, 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3). Exemplary HVRs herein include:

(a) hypervariable loops occurring at amino acid residues 26-32 (L1), 50-52 (L2), 91-96 (L3), 26-32 (H1), 53-55 (H2), and 96-101 (H3) (Chothia and Lesk, J. Mol. Biol. 196:901-917 (1987));

(b) CDRs occurring at amino acid residues 24-34 (L1), 50-56 (L2), 89-97 (L3), 31-35b (H1), 50-65 (H2), and 95-102 (H3) (Kabat et al., Sequences ofProteins ofImmunologicalInterest, 5th Ed. Public Health Service, National Institutes of Health, Bethesda, MD (1991));

(c) antigen contacts occurring at amino acid residues 27c-36 (L1), 46-55 (L2), 89-96 (L3), 30-35b (H1), 47-58 (H2), and 93-101 (H3) (MacCallum et al. J. Mol. Biol. 262: 732-745 (1996)); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

The HVR residues can be identified on websites, e.g. https://www.novopro.en/tools/edr.html.

Unless otherwise indicated, HVR residues and other residues in the variable domain (e.g., FR residues) are numbered herein according to Kabat et al., supra.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). See, e.g., Kindt et al. *Kuby Immunology,* $6^{th}$ ed., W.H. Freeman and Co., page 91 (2007). A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "vector", as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vector".

II. Exemplary Antibodies

The invention provides an isolated monoclonal antibody, particularly Fc-engineered, that specifically binds to human CLDN18.2, wherein the antibody comprises a VH comprising a HVR-H1 as set forth in SEQ ID NO: 11, a HVR-H2 as set forth in SEQ ID NO: 12 and a HVR-H3 as set forth in SEQ ID NO: 13, and a VL comprising a HVR-L1 as set forth in SEQ ID NO: 14, a HVR-L2 as set forth in SEQ ID NO: 15 and a HVR-L3 as set forth in SEQ ID NO: 16. In one embodiment, the antibody comprises a VH as set forth in SEQ ID NO: 1 and a VL as set forth in SEQ ID NO: 2. Optionally, the first two N-terminal amino acid residues of the VH are absent.

The invention provides an isolated monoclonal antibody, particularly Fc-engineered, that specifically binds to human CLDN18.2, wherein the antibody comprises a VH comprising a HVR-H1 as set forth in SEQ ID NO: 17, a HVR-H2 as set forth in SEQ ID NO: 18 and a HVR-H3 as set forth in SEQ ID NO: 19, and a VL comprising a HVR-L1 as set forth in SEQ ID NO: 20, a HVR-L2 as set forth in SEQ ID NO: 21 and a HVR-L3 as set forth in SEQ ID NO: 22. In one embodiment, the antibody comprises a VH as set forth in SEQ ID NO: 3 and a VL as set forth in SEQ ID NO: 4. Optionally, the first two N-terminal amino acid residues of the VH are absent.

The invention provides an isolated monoclonal antibody, particularly Fc-engineered, that specifically binds to human CLDN18.2, wherein the antibody comprises a VH comprising a HVR-H1 as set forth in SEQ ID NO: 23, a HVR-H2 as set forth in SEQ ID NO: 24 and a HVR-H3 as set forth in SEQ ID NO: 25, and a VL comprising a HVR-L1 as set forth in SEQ ID NO: 26, a HVR-L2 as set forth in SEQ ID NO: 27 and a HVR-L3 as set forth in SEQ ID NO: 28. In one embodiment, the antibody comprises a VH as set forth in SEQ ID NO: 5 and a VL as set forth in SEQ ID NO: 6. Optionally, the first two N-terminal amino acid residues of the VH are absent.

The invention provides an isolated monoclonal antibody, particularly Fc-engineered, that specifically binds to human CLDN18.2, wherein the antibody comprises a VH comprising a HVR-H1 as set forth in SEQ ID NO: 29, a HVR-H2 as set forth in SEQ ID NO: 30 and a HVR-H3 as set forth in SEQ ID NO: 31, and a VL comprising a HVR-L1 as set forth in SEQ ID NO: 32, a HVR-L2 as set forth in SEQ ID NO: 33 and a HVR-L3 as set forth in SEQ ID NO: 34.

The invention provides an isolated monoclonal antibody, particularly Fc-engineered, that specifically binds to human CLDN18.2, wherein the antibody comprises a VH comprising a HVR-H1 as set forth in SEQ ID NO: 41, a HVR-H2 as set forth in SEQ ID NO: 42 and a HVR-H3 as set forth in SEQ ID NO: 43, and a VL comprising a HVR-L1 as set forth in SEQ ID NO: 44, a HVR-L2 as set forth in SEQ ID NO: 45 and a HVR-L3 as set forth in SEQ ID NO: 46. The invention provides an isolated monoclonal antibody, particularly Fc-engineered, that specifically binds to human CLDN18.2, wherein the antibody comprises a VH comprising a HVR-H1 as set forth in SEQ ID NO: 47, a HVR-H2 as set forth in SEQ ID NO: 48 and a HVR-H3 as set forth in SEQ ID NO: 49, and a VL comprising a HVR-L1 as set forth in SEQ ID NO: 50, a HVR-L2 as set forth in SEQ ID NO: 51 and a HVR-L3 as set forth in SEQ ID NO: 52. The invention provides an isolated monoclonal antibody, particularly Fc-engineered, that specifically binds to human CLDN18.2, wherein the antibody comprises a VH comprising a HVR-H1 as set forth in SEQ ID NO: 53, a HVR-H2 as set forth in SEQ ID NO: 54 and a HVR-H3 as set forth in SEQ ID NO: 55, and a VL comprising a HVR-L1 as set forth in SEQ ID NO: 56, a HVR-L2 as set forth in SEQ ID NO: 57 and a HVR-L3 as set forth in SEQ ID NO: 58. In one embodiment, the antibody comprises a VH as set forth in SEQ ID NO: 7 and a VL as set forth in SEQ ID NO: 8. Optionally, the first two N-terminal amino acid residues of the VH are absent.

In one embodiment, the one or more mutations in the Fc region are one or more mutations that modify, e.g., increase or decrease, binding to an Fc receptor and/or effector function, e.g., ADCC and/or CDC. In one embodiment, the one or more mutations in the Fc region are one or more substitutions selected from the group consisting of L235V, F243L, R292P, Y300L and P396L. In one embodiment, the one or more mutations in the Fc region are L235V, F243L, R292P, Y300L and P396L.

In one embodiment, the anti-CLDN18.2 monoclonal antibody according to the invention is a murine, chimeric, or humanized antibody.

In one embodiment, the anti-CLDN18.2 monoclonal antibody according to the invention is an antigen-binding antibody fragment, optionally selected from the group consisting of a Fab fragment, a Fab' fragment, a $F(ab')_2$ fragment, a scFv fragment, and a diabody.

In one embodiment, the anti-CLDN18.2 monoclonal antibody according to the invention is a full length antibody. In one embodiment, the anti-CLDN18.2 monoclonal antibody according to the invention comprises a human IgG, particularly IgG1, heavy chain constant region, optionally as set forth in SEQ ID NO: 9. In one embodiment, the anti-CLDN18.2 monoclonal antibody according to the invention comprises a mutated human IgG, particularly IgG1, heavy chain constant region, optionally as set forth in SEQ ID NO: 40. In one embodiment, the anti-CLDN18.2 monoclonal antibody according to the invention comprises a human kappa light chain constant region, optionally as set forth in SEQ ID NO: 10. In one embodiment, the anti-CLDN18.2 monoclonal antibody according to the invention is a chimeric antibody, e.g., a murine/human chimeric antibody. In one embodiment, the anti-CLDN18.2 monoclonal antibody according to the invention is Fc-engineered.

In one embodiment, the monoclonal antibody (mAb) or Fab fragment of the present invention has a crossover format (x-mAb or x-Fab), wherein either the variable domains or the (first) constant domains of the light and heavy chains are exchanged.

III. Recombinant Methods and Compositions

Antibodies may be produced using recombinant methods and compositions, e.g., as described in U.S. Pat. No. 4,816,567. For these methods one or more isolated nucleic acid(s) encoding an antibody are provided.

In case of a native antibody or native antibody fragment two nucleic acids are required, one for the light chain or a fragment thereof and one for the heavy chain or a fragment thereof. Such nucleic acid(s) encode an amino acid sequence comprising the VL and/or an amino acid sequence comprising the VH of the antibody (e.g., the light and/or heavy chain(s) of the antibody). These nucleic acids can be on the same expression vector or on different expression vectors.

In one embodiment isolated nucleic acids encoding an antibody as used in the methods as reported herein are provided.

In a further embodiment, one or more vectors (e.g., expression vectors) comprising such nucleic acid(s) are provided.

In a further embodiment, a host cell comprising such nucleic acid(s) is provided.

In one such embodiment, a host cell comprises (e.g., has been transformed with):

(1) a vector comprising nucleic acids that encode an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody.

In one embodiment, the host cell is eukaryotic, e.g. a Chinese Hamster Ovary (CHO) cell or lymphoid cell (e.g., Y0, NS0, Sp2/0 cell). In one embodiment, a method of making an antibody is provided, wherein the method comprises culturing a host cell comprising nucleic acids encoding the antibody, as provided above, under conditions suitable for expression of the antibody, and optionally recovering the antibody from the host cell or host cell culture medium.

For recombinant production of an antibody, nucleic acids encoding an antibody, e.g., as described above, are isolated and inserted into one or more vectors for further cloning and/or expression in a host cell. Such nucleic acids may be readily isolated and sequenced using conventional procedures (e.g., by using oligonucleotide probes that are capable of binding specifically to genes encoding the heavy and light chains of the antibody) or produced by recombinant methods or obtained by chemical synthesis.

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. See also Charlton, K. A., In: Methods in Molecular Biology, Vol. 248, Lo, B. K. C. (ed.), Humana Press, Totowa, NJ (2003), pp. 245-254, describing expression of antibody fragments in *E. coli*. After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, T. U., Nat. Biotech. 22 (2004) 1409-1414; and Li, H. et al., *Nat. Biotech.* 24 (2006) 210-215.

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham, F. L. et al., J. Gen Virol. 36 (1977) 59-74); baby hamster kidney cells (BHK); mouse sertoli cells (TM4 cells as described, e.g., in Mather, J. P., Biol. Reprod. 23 (1980) 243-252); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather, J. P. et al., Annals N.Y Acad. Sci. 383 (1982) 44-68; MRC 5 cells; and FS4 cells. Other useful mammalian host cell lines include Chinese hamster ovary (CHO) cells, including DHFR-CHO cells (Urlaub, G. et al., Proc. Natl. Acad. Sci. USA 77 (1980) 4216-4220); and myeloma cell lines such as Y0, NS0 and Sp2/0. For a review of certain mammalian host cell lines suitable for antibody production, see, e.g., Yazaki, P. and Wu, A. M., Methods in Molecular Biology, Vol. 248, Lo, B. K. C. (ed.), Humana Press, Totowa, NJ (2004), pp. 255-268.

IV. Assays

Antibodies provided herein may be identified, screened for, or characterized for their physical/chemical properties and/or biological activities by various assays known in the art.

Binding Assays and Other Assays

In one aspect, an antibody of the invention is tested for its antigen binding activity, e.g., by known methods such as ELISA, Western blot, etc.

In another aspect, competition assays may be used to identify an antibody that competes with aCLDN18.2 for binding to CLDN18.2. In certain embodiments, such a competing antibody binds to the same epitope (e.g., a linear or a conformational epitope) that is bound by aCLDN18.2. Detailed exemplary methods for mapping an epitope to which an antibody binds are provided in Morris (1996) "Epitope Mapping Protocols," in *Methods in Molecular Biology* vol. 66 (Humana Press, Totowa, NJ).

In an exemplary competition assay, immobilized CLDN18.2 is incubated in a solution comprising a first labeled antibody that binds to CLDN18.2 and a second unlabeled antibody that is being tested for its ability to compete with the first antibody for binding to CLDN18.2. The second antibody may be present in a hybridoma supernatant. As a control, immobilized CLDN18.2 is incubated in a solution comprising the first labeled antibody but not the second unlabeled antibody. After incubation under conditions permissive for binding of the first antibody to CLDN18.2, excess unbound antibody is removed, and the amount of label associated with immobilized CLDN18.2 is measured. If the amount of label associated with immobilized CLDN18.2 is substantially reduced in the test sample relative to the control sample, then that indicates that the second antibody is competing with the first antibody for binding to CLDN18.2. See Harlow and Lane (1988) *Antibodies: A Laboratory Manual* ch. 14 (Cold Spring Harbor Laboratory, Cold Spring Harbor, NY).

Activity Assays

In one aspect, assays are provided for identifying anti-CLDN18.2 antibodies thereof having biological activity. Biological activity may include, e.g., effect of anti-CLDN18.2 antibodies on ADCC by PBMC on target cells expressing CLDN18.2. Antibodies having such biological activity in vivo and/or in vitro are also provided.

EXAMPLES

After initial screening, four positive hybridoma cell lines from immunized mice were identified with specific binding to the CLDN18.2-expressing cells but not to the CLDN18.1-expressing cells.

Example 1: Cloning Four CLDN18.2 Specific Monoclonal Antibodies (mAbs) from Mouse Hybridoma Cells This example illustrates cloning of the antibody's H and L chain genes out from the mouse hybridoma cells to obtain variable region sequences specific for CLDN18.2 to produce the chimeric antibodies.

Following conventional procedures in the art, RNA was isolated and purified from the hybridoma cells using Quick-RNA™ Microprep Kit (ZYMO Research, Cat. #R1050). First-strand cDNA was synthesized and RACE was performed using SMARTer® RACE 5'/3' kit (Takara Bio USA, Inc. Cat. #634858) together with the IgG1 3' constant primer (SEQ ID NO: 35), the IgG2a 3' constant primer (SEQ ID NO: 36) and the Kappa 3' constant primer (SEQ ID NO: 37). The RACE DNA products were subjected to gel extraction with the NuceloSpin Gel and PCR Clean-Up kit (Takara, Cat. #740986.20). The in-fusion reaction mixture of linearized pRACE vector and gel-purified PACE product was transformed into the Stellar competent cells (Clontech, Cat. #636766). Plasmid DNA was isolated from the transformants using QIAprep Spin Miniprep Kit (Qiagen, Cat. #27104) and subjected to Sanger sequencing (GENEWIZ) using the M13 sequencing primers. The final gene sequences of four pairs of heavy and light chains were obtained (data not shown) which were determined below as the CLDN18.2 mAbs (mAb1, mAb2, mAb3, and mAb4).

Example 2: Constructing Chimeric Antibodies to Replace the Mouse Constant Region with the One from Human This example illustrates construction of chimeric antibodies by replacing the constant regions of the 4 molecularly cloned mouse mAbs with those from human IgG1 heavy chain and kappa light chain.

The plasmid pFUSE-CHIg-hG1 (InvivoGen, Cat #pfuse-hchgl) that contains the constant region of human IgG1 heavy chain (SEQ ID NO: 9) and the plasmid pFUSE2-CLIg-hk (InvivoGen, Cat #pfuse2-hclk) that contains the constant region of human kappa light chain (SEQ ID NO: 10) were digested with Hind III and either Nhe I for IgG1 or BsiW I for kappa (all from NEB lab). The linearized plasmids were purified by gel purification using NucleoSpin Gel and PCR Clean-up kit (Takara, Cat. #740986.20). The coding sequences for the mouse heavy and light chain variable regions of mAb1, mAb2, mAb3, and mAb4 were PCR amplified using HiFi HotStart (Kapa (Roche), KK2602) from the plasmids obtained in Example 1 together with specific primers (data not shown), and purified by gel purification using NucleoSpin Gel and PCR Clean-up kit (Takara, Cat. #740986.20). The linearized vector and the insert fragment were assembled using Gibson Assembly® HiFi 1 Step Kit (SGI (VWR), Cat. #GA1100-50). The assembly reaction mixture was transformed into the Stellar competent cells (Clontech, Cat. #636766). Plasmid DNA was isolated from the transformants using QIAprep Spin Miniprep Kit (Qiagen, Cat. #27104) and subjected to Sanger sequencing (GENEWIZ). Four chimeric antibodies were constructed, with each including the variable region from one of the four mouse mAbs produced in Example 1. The new chimeric antibodies are assigned as. YL-G1-19-01, YL-G1-19-02, YL-G1-19-03, and YL-G1-19-04.

Example 3: Confirming the Specificity of these Four Chimeric Monoclonal Antibodies Via Surface Staining This example illustrates the test of 4 chimeric monoclonal antibodies with their CLDN18.2 binding specificity in comparison with the reference mAb (IMAB362, Ganymed).

CLDN18.2-expressing 293T cells and CLDN18.1-expressing 293T cells at a density of $2\times10^6$ cells/ml in FACS buffer (50 pL) were mixed with a dilution series (60.00, 20.00, 6.67, 2.22, 0.74, 0.25, 0.08 g/mL in FACS buffer) of the chimeric antibodies, the reference antibody, or a IgG negative control (50 μL) in a 96-well V-bottom plate and incubated for 30 min on ice. After a wash with 200 μL/well FACS buffer, cells were resuspended in 30 μL/well secondary antibody Alexa Fluor® 647 AffiniPure Goat Anti-Human IgG, Fcγ fragment specific (Jackson, Cat. #109-605-098) and incubated for 20 min on ice. After three washes with 200 μL/well FACS buffer, cells were resuspended with 150 μl/well FACS buffer and subjected to FACS using BD LSR II Flow Cytometer (HTS). Geometric mean was used for data analysis and plots were made using Prism GraphPad. Flow cytometry analysis showed that 4 chimeric antibodies have higher specific binding to CLDN18.2-expressing cells, comparing to the reference mAb (see FIG. 2). No binding to CLDN18.1-expressing cells was shown (see FIG. 3), suggesting the high specificity of these four chimeric antibodies.

Example 4: Identifying the Functional Activities of these Four Chimeric Antibodies by ADCC Assay This example illustrates the test of the ADCC-mediated killing activity of these 4 chimeric antibodies in comparison with reference mAb (IMAB362, Ganymed).

CLDN18.2-expressing 293T cells and CLDN18.1-expressing 293T cells were labeled with CFSE using eBioscience™ CFSE (Thermo, Cat. #65-0850-84). CFSE labeled cells at a density of $4\times10^5$ cells/ml in Lympholyte® Cell Separation Media (Cedarlane, Cat. #CL5110) (50 μL) were mixed with a dilution series (20.00, 6.67, 2.22, 0.74, 0.25, 0.08, 0.03 g/mL in the medium) of the chimeric antibodies, the reference antibody, or a IgG negative control (100 μL) in a 96-well V-bottom plate and incubated for 15 min at RT in the dark. Then, PBMC at a density of $5\times10^6$ cells/ml (50 μL) was added and the plate was incubated for 2 hours at 37° C. in the dark. Cells were washed twice with PBS and 100 μL working solution of eBioscience™ Fixable Viability Dye eFluor™ 660 (Thermo, Cat. #65-0864) was added to per well. The plate was incubated 30 minutes on ice in the dark. After wash with PBS, cells were resuspended by adding 75 μL/well PBS and 25 μL/well 4% paraformaldehyde and subjected to FACS using BD LSR II Flow Cytometer (HTS). Percentage of killing (CFSE/FVD-AF660 double positive population over CFSE positive population) was used for data analysis and plots were made using Prism GraphPad. ADCC activity by the FACS-based method showed that 4 chimeric antibodies can mediate ADCC activities against the CLDN18.2-expressing cells (see FIG. 4).

Example 5: Characterizing the Fc-Engineered Chimeric Antibodies

Additionally, four Fc-engineered chimeric antibodies were constructed. As compared with the $1^{st}$ generation, initial chimeric antibodies YL-G1-19-01, YL-G1-19-02, YL-G1-19-03, and YL-G1-19-04, the $2^{nd}$ generation, Fc-engineered chimeric antibodies YL-G2-A, YL-G2-B, YL-G2-C and YL-G2-D (in YL-G2-D, the first two N-terminal amino acid residues of the VH domain are absent as compared with YL-G1-19-04) comprise five substitutions in the Fc region, namely L235V, F243L, R292P, Y300L, and P396L, according to the EU numbering. The mutant constant region (including CH1, hinge, CH2, and CH3) of human IgG1 heavy chain is set forth in SEQ ID NO: 40.

This example illustrates the characterization of these Fc-engineered chimeric antibodies.

5.1: Antigen-Antibody Binding Interaction

This example illustrates the characterization of the antigen-antibody binding interaction of YL-G2-B, YL-G2-C and YL-G2-D.

The in vitro biological activity of YL-G2-B, YL-G2-C and YL-G2-D were analyzed by monitoring the binding to recombinant huCLDN18.2-Fc and CHO cells over-expressing huCLDN18.2 by using KinExA 4000 system (KinExA, US).

To determine affinity using the KinExA method, a serial dilution of binding partner B (known as titrant) is performed in the background of binding partner A (known as the constant binding partner, CBP). This means the CBP will remain at a constant concentration, while the titrant will vary in concentration. Once these solutions come to equilibrium, the KinExA 4000 instrument can directly measure the amount of unbound, or free binding partner of CBP left in solutions. Using Sapidyne's software, the percent free of CBP can be plotted against the total titrant concentration to generate a binding curve and determine affinity.

Figure 5:
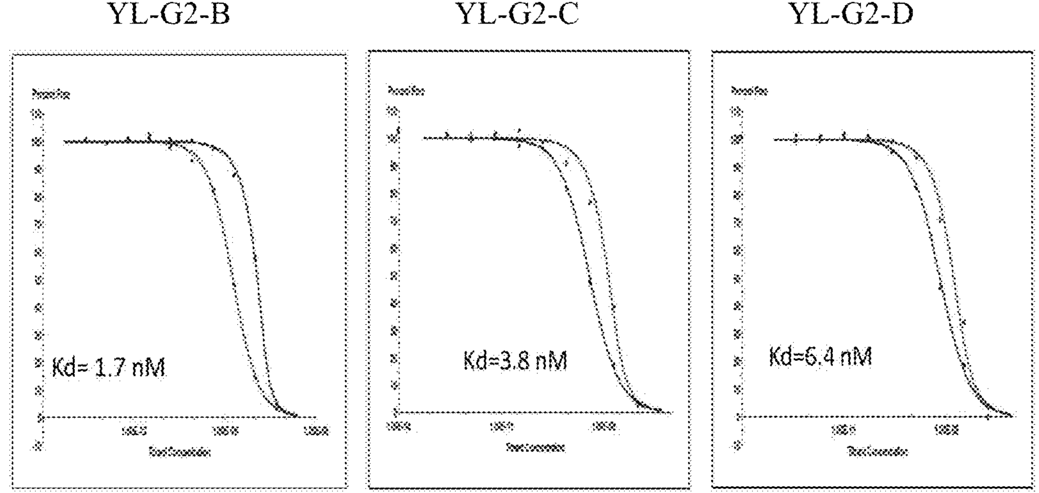
FIG. 5 shows the binding curve to huCLDN18.2 of the antibodies of the present invention.

Kd was first determined with the antibodies and recombinant human CLDN18.2 purchased from Sino Biological (P/N: 20047-H02H). For the equilibrium experiment, the titrant (huCLDN18.2) was serially diluted five-fold in a background of CBP. Two equilibrium experiments were performed one with a high concentration of CBP at 10 nM (20 nM binding sites) with 150 nM of titrant serially diluted five-fold and one with a low concentration of CBP at 100 pM (200 pM binding sites) with 150 nM of titrant serially diluted five-fold. Data was collected on a KinExA 4000 and analyzed using Sapidyne Instruments n-Curve Analysis Software version 4.4.26. The binding curves are shown in FIG. 5.

Figure 6:
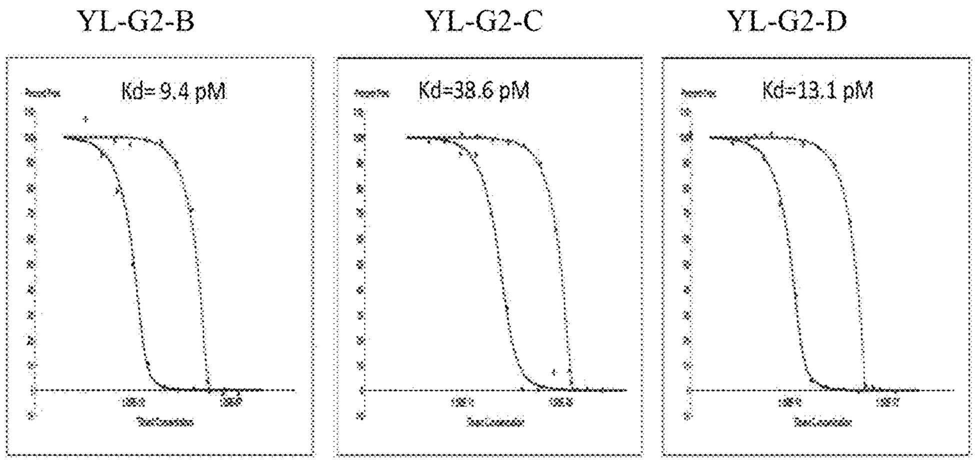
FIG. 6 shows the binding curve to huCLDN18.2-expressing cells of the antibodies of the present invention.

A KinExA 4000 instrument was also used to measure binding affinity of the antibodies to surface protein of intact cells, i.e., CHO cells over-expressing huCLDN18.2. Concentration of the antibodies was held constant (CBP) and concentration of whole cells with surface protein were varied (titrant). Concentration of whole cells with surface proteins were diluted three-fold. Titrated cells were incubated with the constant binding partner (CBP). Once equilibrium was reached, the samples were centrifuged, the supernatants were recovered, and the free CBP was detected with a fluorescently labeled anti-CBP molecule. The binding curves are shown in FIG. 6.

To establish a more accurate Kd, two equilibrium curves were prepared and analyzed. One curve with low concentration of CBP at 100 pM (200 pM binding sites) and $10^6$ cells/mL with three-fold dilutions, and one curve with high concentration of CBP at 10 nM (20 nM binding sites) and $10^6$ cells/mL with three-fold dilutions. The KinExA 4000 measured the amount of unbound CBP in solution. Analysis was performed using Sapidyne Instruments n-Curve Analysis Software version 4.4.26. The summary of equilibrium dissociation constant Kd is shown in Table 1.

TABLE 1

Kd values of YL-G2-B, YL-G2-C and YL-G2-D

| ID | Binding to recombinant huCLDN18.2-Fc (nM) | Binding to CHO cells over-expressing huCLDN18.2 (pM) |
|---|---|---|
| YL-G2-B | 1.7 | 9.4 |
| YL-G2-C | 3.8 | 38.6 |
| YL-G2-D | 6.4 | 13.1 |

5.2: Cell Binding Assay

This example illustrates the cell binding assay of YL-G2-B, YL-G2-C and YL-G2-D.

CHO cells expressing huCLDN18.2 were used to assess the binding of the antibodies. Cells were seeded at $5\times10^5$ cells per 100 μl into a well of a 96-well plate for each sample. Then, 100 μl of each serially diluted antibody was added to the cells, each dilution started at 40 μg/ml and was diluted 5-fold. Therefore, the final concentration of each antibody starts at 20 μg/ml followed by a 5-fold serial dilution. After 1 hour, the cells were washed twice and 100 μl of GAH-FITC (1:200 dilution) was added to each well. After 30 minutes, the cells were washed twice and resuspended in 120 μl of FACS buffer. The cells were analyzed via flow cytometry.

Figure 7:
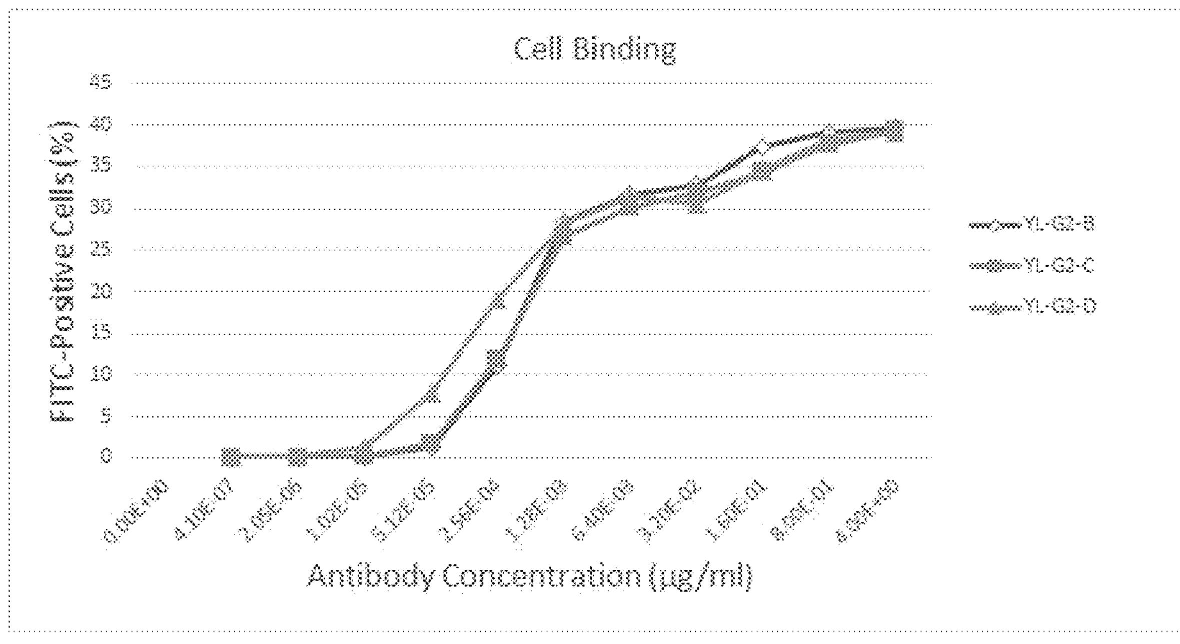
FIG. 7 shows the results of the ADCC assay of the antibodies of the present invention.

Unstained cells were used as a reference to set up overall target cell gating and to establish the FITC-negative populations, allowing us to establish the FITC-positive cell gate for each cell line. Additionally, the mean fluorescence intensity (MFI) of the entire population of cells was calculated to secondarily validate the FITC-positive results. The ratio of the gated positive cell number to the total live cell number is taken as the percentage of positive cells. The results are shown in FIG. 7.

5.3: Complement Dependent Cytotoxicity (CDC) Assay

This example illustrates the complement dependent cytotoxicity (CDC) assay of YL-G2-B, YL-G2-C and YL-G2-D.

Figure 8:
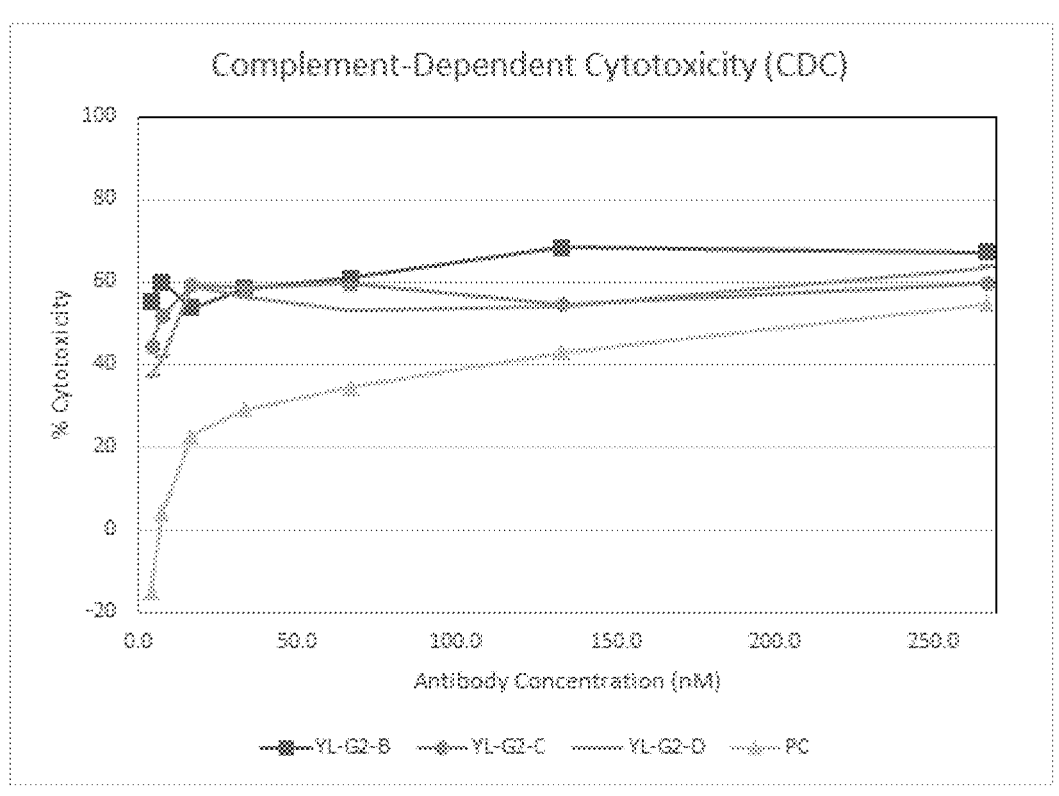
FIG. 8 shows the results of the cell binding assay of the antibodies of the present invention.

The target cells (i.e., CHO cells expressing huCLDN18.2) were washed once with DPBS. The cells were then seeded into a U-bottomed plate at $2\times10^4$ cells, 100 μL/well in RPMI. The antibodies were serially diluted at 1:2 and co-incubated with the cells at 50 μl/well for 15 minutes at room temperature. Then 20% pooled serum at 50 μl/well was added to all the wells, including the spontaneous release and maximum release wells. The plate was incubated in an incubator at 37° C. for 3.5 hours. Forty-five minutes before the end of the incubation period, the plate was centrifuged at 1200 rpm for 5 minutes and 20 μL of Lysis buffer (CyQUANT™ LDH Cytotoxicity Assay Kit, Cat. #C20300 and C20301) was added only to the maximum release control well containing the target cells. Fifty L of the supernatant was transferred into a black-walled 96-well plate, along with 50 μL/well of Reaction buffer (CyQUANT™ LDH Cytotoxicity Assay Kit, Cat. #C20300 and C20301), which was added to all wells, maximum release and spontaneous release wells as well. The plate was incubated in dark for 30 minutes. At the end of the incubation, 50 μL of Stop solution (CyQUANT™ LDH Cytotoxicity Assay Kit, Cat. #C20300 and C20301) was added to all the wells and mixed with gentle by tapping. The OD was measured at 490 nm and 680 nm. The activity was percentage of cytotoxicity: % Cytotoxicity=(experimental value−target cell spontaneous, no vol correction)/(target cell max release−target cell spontaneous, vol corrected)*100. The results are shown in FIG. 8.

5.4: Internalization Assay

This example illustrates the internalization assay of YL-G2-B, YL-G2-C and YL-G2-D.

Figure 9:
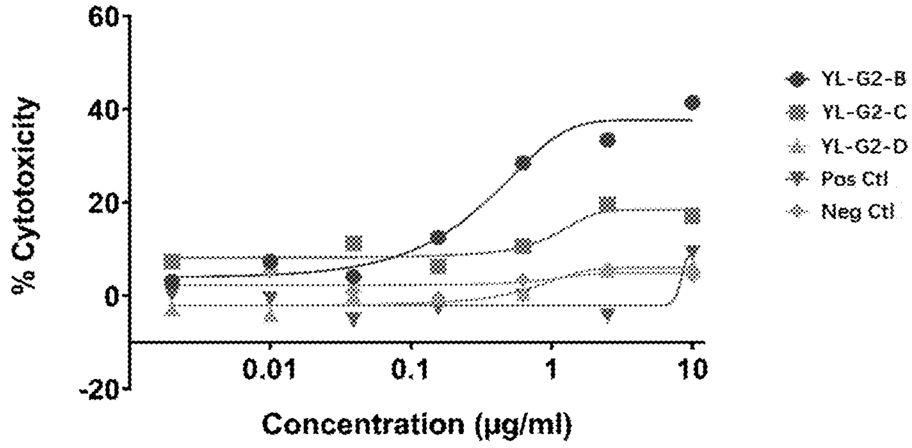
FIG. 9 shows the results of the CDC assay of the antibodies of the present invention.

CHO cells expressing huCLDN18.2 were prepared at $5\times10^5$/mL in DMEM media. Seed 100 μL of cells in each well of U-bottom 96-well plate. Dilute the test antibodies and control antibodies to 40 μg/ml, then serially dilute each antibody in culture media at 1:4. Add each diluted antibody to the cells at 50 μl/well. Incubate the plate at 37° C. for 30 minutes. Then, add 40 μg/ml PEP-ZAP (a small Fc-binding peptide fused with a cell toxic peptide, developed by AB Studio Inc.; see WO 2020/018732 A1) into each well at 50 μl/well for a final concentration of PEP-ZAP at 10 μg/ml. Incubate the plate at 37° C. for 72 hours. Finally, spin the cells and take 100 μl of supernatant for LDH measurement. The results are shown in FIG. 9.

5.5: Antibody Dependent Cell Mediated Cytotoxicity (ADCC) Assay

This example illustrates the antibody dependent cell mediated cytotoxicity (ADCC) assay.

Target (CHO cells expressing huCLDN18.2) and effector cells (NK 8837-F cells, ATCC PTA-8837) were used to assess the ADCC function of the antibodies. Target cells were seeded at $2\times10^4$ cells per 50 μl into a well of a 96-well plate for each sample in DMEM-F12+10% FBS medium. Then, 100 μl of each 1:10 serially diluted antibody was added to the cells. After 20 minutes, NK cells were added onto the plate at $2\times10^5$ cells per 50 μl, resulting in a target:effector ratio of 1:10. After this addition, the resulting final concentration of each antibody started at 50 g/ml, followed by 5, 0.5 and 0.05 g/ml. The plate was placed in a 37° C., $CO_2$ incubator for 24 hours. Then, the cells were stained with 7AAD, washed twice, and resuspended in about 200 μl of FACS buffer. The cells were analyzed via flow cytometry.

Unstained cells were used as a reference to set up overall target cell gating and to establish 7AAD negative populations, allowing differentiation between 7AAD (dead cells) and live cells.

CT26 cells expressing huCLDN18.2 can also be used as the target cells, and ADCC can also be determined via LDH.

Figure 10:
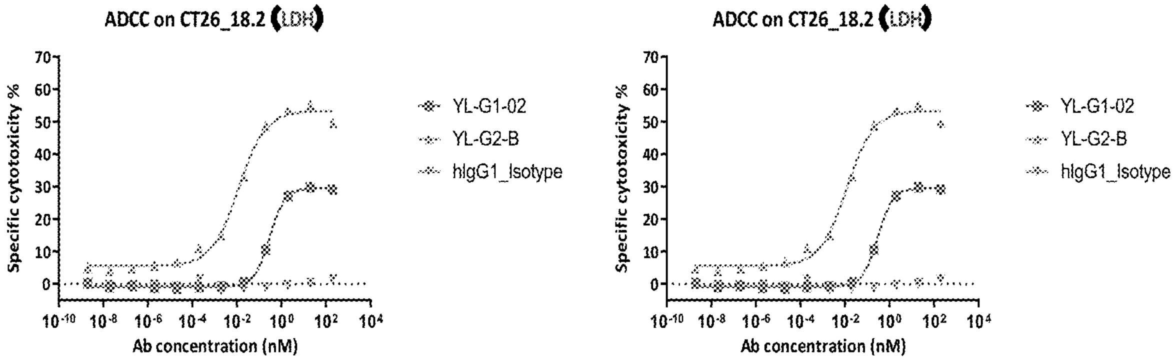
FIG. 10 shows the results of the ADCC assay of the antibodies of the present invention.

A comparison of the ADCC activity between YL-G1-02 and YL-G2-B (having the same amino acid sequence, except for the VLPLL substitutions in the Fc region) is shown in FIG. 10. The summary of EC50 is shown in Table 2.

TABLE 2

ADCC of YL-G1-02 vs YL-G2-B

| ID | LDH | | FACS | |
|---|---|---|---|---|
| | EC50 (nM) | Max (%) | EC50 (nM) | Max (%) |
| YL-G1-02 | 0.30 | 29.8 | ~0.2244 | 32.0 |
| YL-G2-B | 0.012 | 55.1 | 0.0073 | 44.1 |
| isotype | NA | 1.5 | NA | 8.3 |

Example 6: Functional Characterizing the Antibodies 6.1: Cells

CT26 CLDN18.2 cells (mouse colon cancer cells, Kyinno biotechnology, Cat. No. KC-1195) maintained in DMEM medium (Gibco, Cat. No. 31053-036) containing 10% FBS (ExCell Bio, Cat. No. FND500), KATOIII CLDN18.2 cells (human gastric cancer cells, Kyinno biotechnology, Cat. No. KC-1453) maintained in RPMI1640 medium (Gibco, Cat. No. 22400-089) containing 10% FBS and NCI-N87 CLDN18.2 cells (human gastric cancer cells, Kyinno biotechnology, Cat. No. KC-1222) maintained in RPMI1640 medium containing 10% FBS are all tumor cells overexpressing human CLDN18.2 and were used for determining the CDC activity and the ADCC activity of the subject antibodies.

6.2: CDC Assay

The CDC activity of the subject antibodies was evaluated by measuring the change in the level of LDH released into the culture medium after cell lysis. CT26 CLDN18.2 cells or KATOIII CLDN18.2 cells were suspended in RPMI 1640 medium with no phenol red (Gibco, Cat. No. 11835-030) containing 1% FBS at a density of 4E+05 cells/ml or 6E+05 or 1E+06 cells/ml, respectively. The subject antibodies were diluted with RPMI 1640 medium with no phenol red containing 1% FBS to 200, 50, 12.5, 3.13, 0.78, 0.195, 0.0488, 0.0122, 0.00305, 0.000763, and 0.000191 nM. Normal human serum complement (Quidel, Cat. No. A113) were diluted with RPMI 1640 medium with no phenol red containing 1% FBS at 1:50. To each well of a round bottom, 96-well microplate (Corning, Cat. No. 3799), 50 μL antibody diluent, 50 μL normal human serum complement diluent and 50 μL tumor cell suspension were added. Human IgG1 isotype antibody was included as negative control. Reference antibody (IMAB362, Ganymed) was included as positive control. The microplate was incubated for 3-4 hours in an incubator set at 37° C. and 5% $CO_2$. After incubation, the release of LDH into the supernatant of the cell culture was detected according to the instructions provided with the LDH cytotoxicity assay kit (Roche, Cat. No. 11644793001). In brief, the microplate was centrifuged (Eppendorf, model 5810R) at 1500 rpm for 5 minutes and 70 μL supernatant was taken from each well and transferred to a well on a new microplate. Then, 50 μL LDH detection substrate was added to each well and the microplate was incubated at room temperature for 0.5-2 hours. The optical density (OD) at 492 nm was detected using SpectraMax M5e (Molecular Devices LLC), with the optical density at 690 nm subtracted ($OD_{492\ nm}-OD_{690\ nm}$). The CDC activity of the subject antibodies was calculated by the percentage of specific cell lysis using the formula below:

$$\text{Specific cell lysis (\%)} = (OD_{antibody+complement+tumor\ cell} - OD_{complement+tumor\ cell})*100/(OD_{tumor\ cell+Triton} - OD_{tumor\ cell}).$$

The data were analyzed by four-parameter nonlinear regression using GraphPad Prism 7 software, and the $EC_{50}$ value was calculated and obtained.

6.3: ADCC Assay

The ADCC activity of the subject antibodies was evaluated by measuring the change in the level of LDH released into the culture medium after cell lysis. NCI-N87 CLDN18.2 cells or KATOIII CLDN18.2 cells were suspended in RPMI 1640 medium with no phenol red at a density of 6E+05 cells/mL. The subject antibodies were diluted with RPMI 1640 medium with no phenol red containing 1% FBS to 20, 4, 0.8, 0.16, 0.032, 0.0064, 1.28E-03, 2.56E-04, 5.12E-05, 1.02E-05, 2.05E-06, 4.10E-07, 8.19E-08, 1.64E-08, 3.28E-09, 6.55E-10, 1.31E-10, 2.62E-11, and 5.24E-12 nM. Fresh human PBMC cells (Saily, from volunteer #XC11057W) were suspended in RPMI 1640 medium with no phenol red containing 1% FBS at a density of 1.2E+07 cells/mL. To each well of a round bottom, 96-well microplate, 50 μL antibody diluent, 50 μL human PBMC cell suspension and 50 μL tumor cell suspension were added. Human IgG1 isotype was included as negative control. Reference mAb (IMAB362, Ganymed) was included as positive control. The microplate was incubated for 4-6 hours in an incubator set at 37° C. and 5% $CO_2$. After incubation, the release of LDH into the supernatant of the cell culture was detected according to the instructions provided with the LDH cytotoxicity assay kit as described above. The ADCC activity of the subject antibodies was calculated by the percentage of specific cell lysis using the formula below:

$$\text{Specific cell lysis (\%)} = (OD_{antibody+PBMC+tumor\ cell} - OD_{PBMC+tumor\ cell})*100/(OD_{tumor\ cell+Triton} - OD_{tumor\ cell}).$$

The data were analyzed by four-parameter nonlinear regression using GraphPad Prism 7 software, and the $EC_{50}$ value was calculated and obtained.

6.4: CDC Effect on CT26 CLDN18.2 Cells by LDH Assay

As shown in FIG. 11 and Table 3, the two batches of YL-G2-B exhibited comparable CDC effect on CT26 CLDN18.2 cells (FIG. 11, panel A). YL-G1-19-02, YL-G2-B, YL-G1-19-03, YL-G2-C, YL-G1-19-04, and YL-G2-D all exhibited stronger CDC effect on CT26 CLDN18.2 cells than the positive control (FIG. 11).

TABLE 3

CDC effect on CT26 CLDN18.2 cells

| | | | CT26 CLDN18.2 | |
|---|---|---|---|---|
| antibody | concentration (mg/mL) | purity (%) | $EC_{50}$ (nM) | max (% cytotoxity) |
| positive control run A | 20.63 | 96.80% | ~11.54 | 72.52 |
| YL-G1-19-02 | 0.74 | 97.30% | 0.26 | 73.44 |
| YL-G2-B batch 1 | 18.96 | 97.90% | 0.14 | 75.99 |
| YL-G2-B batch 2 | 50 | 98.70% | 0.12 | 74.74 |
| hIgG1_Isotype run A | 13.6 | 99.40% | NA | 10.80 |
| positive control run B | 20.63 | 96.80% | ~10.70 | 54.74 |
| YL-G1-19-03 | 10.73 | 96.00% | 0.24 | 62.21 |
| YL-G2-C | 5.55 | 93.22% | 0.10 | 65.24 |
| hIgG1_Isotype run B | 13.6 | 99.40% | NA | −0.23 |
| positive control run C | 20.63 | 96.80% | ~11.86 | 51.65 |
| YL-G1-19-04 | 9.03 | 98.00% | 0.19 | 59.21 |
| YL-G2-D | 4.37 | 98.01% | 0.12 | 71.85 |
| hIgG1_Isotype run C | 13.6 | 99.40% | NA | −0.38 |

6.5: CDC effect on KATOIII CLDN18.2 cells by LDH assay

As shown in FIG. 12 and Table 4, the two batches of YL-G2-B exhibited comparable CDC effect on CT26 CLDN18.2 cells (FIG. 12, panel A). YL-G1-19-02, YL-G2-B, YL-G1-19-03, YL-G2-C, YL-G1-19-04 and YL-G2-D all exhibited stronger CDC effect on KATOIII CLDN18.2 cells than the positive control, positive control (FIG. 12).

TABLE 4

CDC effect on KATOIII CLDN18.2 cells

| | | | KATOIII CLDN18.2 | |
|---|---|---|---|---|
| antibody | concentration (mg/mL) | purity (%) | $EC_{50}$ (nM) | max (% cytotoxity) |
| positive control run A | 20.63 | 96.80% | ~38.08 | 29.71 |
| YL-G1-19-02 | 0.74 | 97.30% | 1.95 | 35.43 |
| YL-G2-B batch 1 | 18.96 | 97.90% | 1.24 | 39.65 |
| YL-G2-B batch 2 | 50 | 98.70% | 1.33 | 39.42 |
| hIgG1_Isotype run A | 13.6 | 99.40% | NA | −0.85 |
| positive control run B | 20.63 | 96.80% | ~22.73 | 45.96 |
| YL-G1-19-03 | 10.73 | 96.00% | ~4.98 | 67.00 |
| YL-G2-C | 5.55 | 93.22% | ~6.04 | 74.56 |
| hIgG1_Isotype run B | 13.6 | 99.40% | NA | −2.46 |
| positive control run C | 20.63 | 96.80% | ~27.48 | 34.89 |
| YL-G1-19-04 | 9.03 | 98.00% | 4.76 | 48.32 |
| YL-G2-D | 4.37 | 98.01% | 2.40 | 49.19 |
| hIgG1_Isotype run C | 13.6 | 99.40% | NA | −1.53 |

6.6: ADCC effect on KATOIII CLDN18.2 cells by LDH assay

As shown in FIG. 13 and Table 5, the two batches of YL-G2-B exhibited comparable ADCC effect on KATOIII CLDN18.2 cells (FIG. 13, panel A). YL-G2-B ($EC_{50}$=0.028 nM or 0.018 nM for different batches), YL-G2-C ($EC_{50}$=0.019 nM) and YL-G2-D ($EC_{50}$=0.021 nM) exhibited stronger ADCC effect (lower $EC_{50}$) and YL-G1-19-02 ($EC_{50}$=0.16 nM), YL-G1-19-03 ($EC_{50}$=0.21 nM) and YL-G1-19-04 ($EC_{50}$=0.14 nM) exhibited comparable ADCC effect on KATOIII CLDN18.2 cells as compared with the positive control ($EC_{50}$=0.12 nM, 0.22 nM or 0.27 nM for three runs) (FIG. 13).

TABLE 5

ADCC effect on KATOIII CLDN18.2 cells

| antibody | concentration (mg/mL) | purity (%) | KATOIII CLDN18.2 EC$_{50}$ (nM) | KATOIII CLDN18.2 max (% cytotoxity) |
|---|---|---|---|---|
| positive control run A | 20.63 | 96.80% | 0.12 | 27.89 |
| YL-G1-19-02 | 0.74 | 97.30% | 0.16 | 19.90 |
| YL-G2-B batch 1 | 18.96 | 97.90% | 0.028 | 19.90 |
| YL-G2-B batch 2 | 50 | 98.70% | 0.018 | 15.78 |
| hIgG1_Isotype run A | 13.6 | 99.40% | NA | 0.3 |
| positive control run B | 20.63 | 96.80% | 0.22 | 24.46 |
| YL-G1-19-03 | 10.73 | 96.00% | 0.21 | 16.72 |
| YL-G2-C | 5.55 | 93.22% | 0.019 | 17.57 |
| hIgG1_Isotype run run B | 13.6 | 99.40% | NA | −5.51 |
| positive control run C | 20.63 | 96.80% | 0.27 | 24.54 |
| YL-G1-19-04 | 9.03 | 98.00% | 0.14 | 15.44 |
| YL-G2-D | 4.37 | 98.01% | 0.021 | 18.42 |
| hIgG1_Isotype run C | 13.6 | 99.40% | NA | −7.64 |

6.7: ADCC effect on NCI-N87 CLDN18.2 cells by LDH assay

As shown in FIG. 14 and Table 6, the two batches of YL-G2-B exhibited comparable ADCC effect on NCI-N87 CLDN18.2 cells (FIG. 14, panel A). YL-G2-B (EC$_{50}$=0.0067 nM or 0.012 nM for different batches), YL-G2-C(EC$_{50}$=0.0078 nM) and YL-G2-D (EC$_{50}$=0.0089 nM) exhibited strongerADCC effect (lower EC$_{50}$) and YL-G-19-02 (EC$_{50}$=0.072 nM), YL-G1-19-03 (EC$_{50}$=0.13 nM) and YL-G1-19-04 (EC$_{50}$=0.067 nM) exhibited comparable ADCC effect on KATOIII CLDN18.2 cells as compared with the positive control (EC$_{50}$=0.057 nM, 0.082 nM or 0.10 nM for three runs) (FIG. 14).

TABLE 6

ADCC effect on NCI-N87 CLDN18.2 cells

| antibody | concentration (mg/mL) | purity (%) | NCI-N87 CLDN18.2 EC$_{50}$ (nM) | NCI-N87 CLDN18.2 max (% cytotoxity) |
|---|---|---|---|---|
| positive control run A | 20.63 | 96.80% | 0.057 | 26.05 |
| YL-G1-19-02 | 0.74 | 97.30% | 0.072 | 16.80 |
| YL-G2-B batch 1 | 18.96 | 97.90% | 0.0067 | 19.04 |
| YL-G2-B batch 2 | 50 | 98.70% | 0.012 | 21.05 |
| hIgG1_Isotype run A | 13.6 | 99.40% | NA | −6.73 |
| positive control run B | 20.63 | 96.80% | 0.082 | 22.06 |
| YL-G1-19-03 | 10.73 | 96.00% | 0.13 | 15.21 |
| YL-G2-C | 5.55 | 93.22% | 0.0078 | 14.93 |
| hIgG1_Isotype run B | 13.6 | 99.40% | NA | −11.72 |
| positive control run C | 20.63 | 96.80% | 0.10 | 21.11 |
| YL-G1-19-04 | 9.03 | 98.00% | 0.067 | 12.59 |
| YL-G2-D | 4.37 | 98.01% | 0.0089 | 18.60 |
| hIgG1_Isotype run C | 13.6 | 99.40% | NA | −9.22 |

6.8: SPR

The binding affinity of the subject antibodies was determined via SPR according to USP 43 IMMUNOLOGICAL TEST METHODS—SURFACE PLASMON RESONANCE <1105> and CP, 2020 edition, Part IV, General Rules, 3429 INMUNOCHIEMISTRY, NON-LABELING IMMUNOCHEMICAL METHODS (IV) SURFACE PLASMON RESONANCE, using Human Antibody Capture Kit, type 2 (Cytiva, Cat. No. 29234600). In brief, an anti-human IgG (Fc) antibody was diluted with the immobilization buffer to 25 g/mL and injected onto a Series S Sensor CM5 chip (Cytiva, Cat. No. BR100530) at a flow rate of 10 μL/minute for 6 minutes to achieve about 7000-14000 response units (RU) of coupled secondary antibody. Then, the subject antibody was diluted with the running buffer to 5 μg/mL and injected at a flow rate of 10 μL/minute to achieve about 200 RU of coupled primary antibody. For kinetics measurements, two-fold serial dilutions (0.195-50 nM) of His-tagged human Claudin-18.2 was injected at a flow rate of 30 μL/minute and binding was monitored for 120 seconds for association and 300 seconds for dissociation on Biacore 8K (Cytiva). Association rates ($k_a$) and dissociation rates ($k_d$) were calculated using a simple one-to-one binding model by simultaneously fitting the association and dissociation sensorgrams. The equilibrium dissociation constant ($K_D$) is calculated as the ratio $k_d/k_a$. The results are shown in Table 7 below.

TABLE 7

| Subject antibody | Capture Level (RU) | $k_a$ (1/Ms) | $k_d$ (1/s) | $K_D$ (M) | Rmax (RU) | Chi$^2$ (RU$^2$) |
|---|---|---|---|---|---|---|
| YL-G1-19-02 | 162.4 | 6.73E+05 | 1.41E−03 | 2.09E−09 | 181.1 | 7.15 |
| YL-G1-19-03 | 163.1 | 4.75E+05 | 5.67E−04 | 1.19E−09 | 167.9 | 1.26 |
| YL-G1-19-04 | 168.6 | 6.28E+05 | 7.80E−04 | 1.24E−09 | 175.1 | 3.30 |
| YL-G2-B | 168.7 | 6.86E+05 | 1.40E−03 | 2.05E−09 | 187.5 | 9.14 |
| YL-G2-C | 160.5 | 5.32E+05 | 5.91E−04 | 1.11E−09 | 177.7 | 3.85 |
| YL-G2-D | 169.4 | 7.07E+05 | 7.22E−04 | 1.02E−09 | 187.2 | 3.67 |

Table of Sequences

| SEQ ID NO | Description | Sequence |
|---|---|---|
| 1 | YL-G1-19-01 VH | QVQLQQSGAELVRPGTSVKVSCKASGYAFTNYLIEWVKQRPGQGLEWIGVINPGSGGTNY NEKFKGKATLTADKSSNTAYMQLSSLTSEDSAVYFCARVYYGNSFGYWGQGTLVTVSA |
| 2 | YL-G1-19-01 VL | DIVMTQSPSSLTVTAGEKVTMSCKSSQSLLNSGNQKNYLTWYQQKPGQPPKLLIYWASTR ESGVPDRFTGSGSGTDFTLTISSVQAEDLAVYYCQNEYFYPFTFGSGTKLEIK |

-continued

Table of Sequences

| SEQ ID NO | Description | Sequence |
|---|---|---|
| 3 | YL-G1-19-02 VH | EVQLQQSGPELEKPGASVKISCKASGYSFTGYKMNWVKQSNGKSLEWIGNIDPYYGGTTY NQKFKGKATLTVDKSSSTAYMQLKSLTSEDSAVYYCARYGKGNTMDYWGQGTSVTVSS |
| 4 | YL-G1-19-02 VL | DIVMTQSPSSLTVTAGEKVTMSCKSSQSLLNSGNQKNYLTWYQQRPGQPPKLLIYWASTR ESGVPVRFTGSGSGTDFTLTISSVQAEDLAVYYCQNAYIYPLTFGTGTKLELK |
| 5 | YL-G1-19-03 VH | QIQLVQSGPELRKPGETVKISCKASGFPFTTDGMSWVKQAPGKGLKWMGWINTYSGVPTY ADDFKGRVAFSLETSASTAYLQIKNLKNEDTATYFCARFRRGNALDNWGQGTSVTVSS |
| 6 | YL-G1-19-03 VL | DIVMTQSPSSLTVTAGEKVTMSCKSSQSLLNSGNQKNYLTWYQQKPGQPPKLLIYWASTR ESGVPDRFTGSGSGTDFTLTISSVQAEDLAIYYCQNNYFYPLTFGAGTRLELK |
| 7 | YL-G1-19-04 VH | EVQLQQSGPELEKPGASVKISCKASGYSFTGYKMNWVKQSNGESLEWIGNIDPYYGDTTY TQKFKGKATFTVDTSSSTAYMQLKSLTSEDSAVYFCARYNRGNTMDYWGQGTSVTVSS |
| 8 | YL-G1-19-04 VL | DIVMTQSPSSLTVTAGEKVTLSCKSSQSLLNSGNQKNYLTWYQQRPGQPPKLLIYWASTR ESGVPVRFTGSGSGADFTLTISSVQAEDLAVYFCQNAYFYPLTFGTGTKLELR |
| 9 | Human IgG1 CH | ASTKGPSVFPLAPSSKSTSGGTAALGCLVKDYFPEPVTVSWNSGALTSGVHTFPAVLQSS GLYSLSSVVTVPSSSLGTQTYICNVNHKPSNTKVDKRVEPKSCDKTHTCPPCPAPELLGG PSVFLFPPKPKDTLMISRTPEVTCVVVDVSHEDPEVKFNWYVDGVEVHNAKTKPREEQYN STYRVVSVLTVLHQDWLNGKEYKCKVSNKALPAPIEKTISKAKGQPREPQVYTLPPSREE MTKNQVSLTCLVKGFYPSDIAVEWESNGQPENNYKTTPPVLDSDGSFFLYSKLTVDKSRW QQGNVFSCSVMHEALHNHYTQKSLSLSPGK |
| 10 | Human kappa CL | RTVAAPSVFIFPPSDEQLKSGTASVVCLLNNFYPREAKVQWKVDNALQSGNSQESVTEQD SKDSTYSLSSTLTLSKADYEKHKVYACEVTHQGLSSPVTKSFNRGEC |
| 11 | YL-G1-19-01 HVR-H1 | GYAFTNYL |
| 12 | YL-G1-19-01 HVR-H2 | INPGSGGT |
| 13 | YL-G1-19-01 HVR-H3 | ARVYYGNSFGY |
| 14 | YL-G1-19-01 HVR-L1 | QSLLNSGNQKNY |
| 15 | YL-G1-19-01 HVR-L2 | WAS |
| 16 | YL-G1-19-01 HVR-L3 | QNEYFYPFT |
| 17 | YL-G1-19-02 HVR-H1 | GYSFTGYK |
| 18 | YL-G1-19-02 HVR-H2 | IDPYYGGT |
| 19 | YL-G1-19-02 HVR-H3 | ARYGKGNTMDY |
| 20 | YL-G1-19-02 HVR-L1 | QSLLNSGNQKNY |
| 21 | YL-G1-19-02 HVR-L2 | WAS |
| 22 | YL-G1-19-02 HVR-L3 | QNAYIYPLT |
| 23 | YL-G1-19-03 HVR-H1 | GFPFTTDG |
| 24 | YL-G1-19-03 HVR-H2 | INTYSGVP |
| 25 | YL-G1-19-03 HVR-H3 | ARFRRGNALDN |

-continued

Table of Sequences

| SEQ ID NO | Description | Sequence |
|---|---|---|
| 26 | YL-G1-19-03 HVR-L1 | QSLLNSGNQKNY |
| 27 | YL-G1-19-03 HVR-L2 | WAS |
| 28 | YL-G1-19-03 HVR-L3 | QNNYFYPLT |
| 29 | YL-G1-19-04 HVR-H1 IMGT | GYSFTGYK |
| 30 | YL-G1-19-04 HVR-H2 IMGT | IDPYYGDT |
| 31 | YL-G1-19-04 HVR-H3 IMGT | ARYNRGNTMDY |
| 32 | YL-G1-19-04 HVR-L1 IMGT | QSLLNSGNQKNY |
| 33 | YL-G1-19-04 HVR-L2 IMGT | WAS |
| 34 | YL-G1-19-04 HVR-L3 IMGT | QNAYFYPLT |
| 35 | IgG1 3' constant primer | GATTACGCCAAGCTTTCATTTACCAGGAGAGTGGGAGAGGCTC |
| 36 | IgG2a 3' constant primer | GATTACGCCAAGCTTTCATTTACCCGGAGTCCGGGAGAAGCTC |
| 37 | Kappa 3' constant primer | GATTACGCCAAGCTTTCAACACTCATTCCTGTTGAAGCTCTTG |
| 38 | huCLDN18.2 (261 aa) | MAVTACQGLG FVVSLIGIAG IIAATCMDQW STQDLYNNPV TAVFNYQGLW RSCVRESSGF TECRGYFTLL GLPAMLQAVR ALMIVGIVLG AIGLLVSIFA LKCIRIGSME DSAKANMTLT SGIMFIVSGL CAIAGVSVFA NMLVTNFWMS TANMYTGMGG MVQTVQTRYT FGAALFVGWV AGGLTLIGGV MMCIACRGLA PEETNYKAVS YHASGHSVAY KPGGFKASTG FGSNTKNKKI YDGGARTEDE VQSYPSKHDY V |
| 39 | huCLDN18.1 (261 aa) | MSTTTCQVVA FLLSILGLAG CIAATGMDMW STQDLYDNPV TSVFQYEGLW RSCVRQSSGF TECRPYFTIL GLPAMLQAVR ALMIVGIVLG AIGLLVSIFA LKCIRIGSME DSAKANMTLT SGIMFIVSGL CAIAGVSVFA NMLVTNFWMS TANMYTGMGG MVQTVQTRYT FGAALFVGWV AGGLTLIGGV MMCIACRGLA PEETNYKAVS YHASGHSVAY KPGGFKASTG FGSNTKNKKI YDGGARTEDE VQSYPSKHDY V |
| 40 | Mutant Human IgG1 CH | ASTKGPSVFPLAPSSKSTSGGTAALGCLVKDYFPEPVTVSWNSGALTSGVHTFPAVLQSS GLYSLSSVVTVPSSSLGTQTYICNVNHKPSNTKVDKRVEPKSCDKTHTCPPCPAPELVGG PSVFLLPPKPKDTLMISRTPEVTCVVVDVSHEDPEVKFNWYVDGVEVHNAKTKPPEEQYN STLRVVSVLTVLHQDWLNGKEYKCKVSNKALPAPIEKTISKAKGQPREPQVYTLPPSREE MTKNQVSLTCLVKGFYPSDIAVEWESNGQPENNYKTTPLVLDSDGSFFLYSKLTVDKSRW QQGNVFSCSVMHEALHNHYTQKSLSLSPGK |
| 41 | YL-G1-19-04 HVR-H1 Kabat | GYKMN |
| 42 | YL-G1-19-04 HVR-H2 Kabat | NIDPYYGDTTYTQKFKG |
| 43 | YL-G1-19-04 HVR-H3 Kabat | YNRGNTMDY |
| 44 | YL-G1-19-04 HVR-L1 Kabat | KSSQSLLNSGNQKNYLT |

-continued

Table of Sequences

| SEQ ID NO | Description | Sequence |
|---|---|---|
| 45 | YL-G1-19-04 HVR-L2 Kabat | WASTRES |
| 46 | YL-G1-19-04 HVR-L3 Kabat | QNAYFYPLT |
| 47 | YL-G1-19-04 HVR-H1 Chothia | GYSFTGY |
| 48 | YL-G1-19-04 HVR-H2 Chothia | DPYYGD |
| 49 | YL-G1-19-04 HVR-H3 Chothia | YNRGNTMDY |
| 50 | YL-G1-19-04 HVR-L1 Chothia | KSSQSLLNSGNQKNYLT |
| 51 | YL-G1-19-04 HVR-L2 Chothia | WASTRES |
| 52 | YL-G1-19-04 HVR-L3 Chothia | QNAYFYPLT |
| 53 | YL-G1-19-04 HVR-H1 Contact | TGYKMN |
| 54 | YL-G1-19-04 HVR-H2 Contact | WIGNIDPYYGDTT |
| 55 | YL-G1-19-04 HVR-H3 Contact | ARYNRGNTMD |
| 56 | YL-G1-19-04 HVR-L1 Contact | LNSGNQKNYLTWY |
| 57 | YL-G1-19-04 HVR-L2 Contact | LLIYWASTRE |
| 58 | YL-G1-19-04 HVR-L3 Contact | QNAYFYPL |

The invention claimed is:

1. A monoclonal antibody which specifically binds to CLDN18.2, comprising:

a HVR-H1, a HVR-H2 and a HVR-H3 comprised in a VH as set forth in SEQ ID NO: 7, and a HVR-L1, a HVR-L2 and a HVR-L3 comprised in a VL as set forth in SEQ ID NO: 8.

2. The monoclonal antibody according to claim 1, comprising:

(1) a HVR-H1 as set forth in SEQ ID NO: 29, a HVR-H2 as set forth in SEQ ID NO: 30, a HVR-H3 as set forth in SEQ ID NO: 31, a HVR-L1 as set forth in SEQ ID NO: 32, a HVR-L2 as set forth in SEQ ID NO: 33, and a HVR-L3 as set forth in SEQ ID NO: 34;

(2) a HVR-H1 as set forth in SEQ ID NO: 41, a HVR-H2 as set forth in SEQ ID NO: 42, a HVR-H3 as set forth in SEQ ID NO: 43, a HVR-L1 as set forth in SEQ ID NO: 44, a HVR-L2 as set forth in SEQ ID NO: 45, and a HVR-L3 as set forth in SEQ ID NO: 46;

(3) a HVR-H1 as set forth in SEQ ID NO: 47, a HVR-H2 as set forth in SEQ ID NO: 48, a HVR-H3 as set forth in SEQ ID NO: 49, a HVR-L1 as set forth in SEQ ID NO: 50, a HVR-L2 as set forth in SEQ ID NO: 51, and a HVR-L3 as set forth in SEQ ID NO: 52; or (4) a HVR-H1 as set forth in SEQ ID NO: 53, a HVR-H2 as set forth in SEQ ID NO: 54, a HVR-H3 as set forth in SEQ ID NO: 55, a HVR-L1 as set forth in SEQ ID NO: 56, a HVR-L2 as set forth in SEQ ID NO: 57, and a HVR-L3 as set forth in SEQ ID NO: 58.

3. The monoclonal antibody according to claim 1, comprising:

a VH as set forth in SEQ ID NO: 7 and a VL as set forth in SEQ ID NO: 8.

4. The monoclonal antibody according to claim 1, which is a full length antibody.

5. The monoclonal antibody according to claim 4, which comprises a human IgG heavy chain constant region and/or a human kappa light chain constant region.

6. The monoclonal antibody according to claim 1, which is an antigen-binding antibody fragment selected from the group consisting of a Fab fragment, a Fab' fragment, a $F(ab')_2$ fragment, a scFv fragment, and a diabody.

7. The monoclonal antibody according to claim 1, which is isolated, naked and/or conjugated.

8. The monoclonal antibody according to claim 4, wherein the monoclonal antibody is Fc-engineered to comprise one or more mutations in the Fc region, and wherein the one or more mutations in the Fc region are one or more substitutions selected from the group consisting of L235V, F243L, R292P, Y300L and P396L.

9. The monoclonal antibody according to claim 4, which comprises an engineered human IgG1 heavy chain constant region as set forth in SEQ ID NO: 40.

10. An isolated nucleic acid encoding the monoclonal antibody according to claim 1.

11. A method of producing the monoclonal antibody according to claim 1 by culturing a host cell comprising a nucleic acid encoding the monoclonal antibody under conditions to produce the antibody.

12. A composition comprising the monoclonal antibody according to claim 1.

13. The monoclonal antibody according to claim 3, which comprises a human IgG1 heavy chain constant region as set forth in SEQ ID NO:9 and a human kappa light chain constant region as set forth in SEQ ID NO:10.

14. The monoclonal antibody according to claim 3, which comprises an engineered human IgG1 heavy chain constant region as set forth in SEQ ID NO:40 and a human kappa light chain constant region as set forth in SEQ ID NO:10.

15. An isolated nucleic acid encoding the monoclonal antibody according to claim 14.

16. A method of producing the monoclonal antibody according to claim 14 by culturing a host cell comprising a nucleic acid encoding the monoclonal antibody under conditions to produce the antibody.

17. A composition comprising the monoclonal antibody according to claim 14.

* * * * *